(12) United States Patent
Williamson et al.

(10) Patent No.: US 8,313,928 B2
(45) Date of Patent: Nov. 20, 2012

(54) EXPRESSION SYSTEM

(75) Inventors: Ethel Diane Williamson, Wiltshire (GB); Julie Miller, Wiltshire (GB); Nicola Jane Walker, Wiltshire (GB); Leslie William James Baillie, Wiltshire (GB); Paula Thomson Holden, Wiltshire (GB); Helen Claire Flick-Smith, Wiltshire (GB); Helen Lisa Bullifent, Wiltshire (GB); Richard William Titball, Wiltshire (GB); Andrew William Topping, North Yorkshire (GB)

(73) Assignee: The Secretary of State for Defense (GB)

( * ) Notice: Subject to any disclaimer, the term of this patent is extended or adjusted under 35 U.S.C. 154(b) by 1493 days.

(21) Appl. No.: 11/728,384

(22) Filed: Mar. 26, 2007

(65) Prior Publication Data

US 2010/0266639 A1   Oct. 21, 2010

Related U.S. Application Data

(62) Division of application No. 10/332,282, filed on Apr. 11, 2003, now Pat. No. 7,537,771.

(30) Foreign Application Priority Data

Jul. 8, 2000   (GB) .................................. 0016702.3

(51) Int. Cl.
*A61K 39/07* (2006.01)
*C12N 15/09* (2006.01)
*C12N 1/21* (2006.01)
*C12N 15/70* (2006.01)
*C07H 21/04* (2006.01)
*C07K 14/32* (2006.01)
*A61P 31/04* (2006.01)

(52) U.S. Cl. ............... 435/69.3; 435/252.33; 435/320.1; 424/246.1; 530/350

(58) Field of Classification Search ........................ None
See application file for complete search history.

(56) References Cited

U.S. PATENT DOCUMENTS

| 5,677,274 A | 10/1997 | Leppla et al. |
| 7,537,771 B2 | 5/2009 | Williamson et al. |
| 2003/0170263 A1 | 9/2003 | Williamson et al. |

FOREIGN PATENT DOCUMENTS

| WO | WO 00/02522 A | 1/2000 |
| WO | WO 02/04646 A1 | 1/2002 |

OTHER PUBLICATIONS

Sharma et al (Protein Expression and Purification, 7, 33-38, 1996).*
Willhite et al (Protein and Peptide Letters, 5(5):273-278, 1998).*
Bowie et al (Science, 1990, 257:1306-1310).*
Cirino, et al., "Disruption of Anthrax Toxin Binding with the Use of Human Antibodies and Competitive Inhibitors", Infection and Immunity 1999, 67(6): 2957-2963.
Flick-Smith, et al., "Protective Efficacy of PA Domains in Mice", Immunology, 101 Supplement 1, 83.
Gouy, et al., "Codon usage in bacteria; correlation with gene expressivity", Nucleic Acids Research 1982, 10(22): 7055-7074.
Gupta, et al., "Expression and purification of the recombinant protective antigen of *Bacillus anthracis*", Protein Expression and Purification 1999, 16(3): 369-376.
Ikemura, "Codon usage and tRNA content in unicellular and multicellular organisms", Molecular Biology and Evolution 1985, 2(1): 13-34.
Little, et al., "Location of receptor-binding region of protective antigen from *Bacillus anthracis*", Biochemical and Biophysical Research Communications 1991, 180(2): 531-537.
Musson, et al., "Differential Processing of CD4 T-cell Epitopes from the Protective Antigen of *Bacillus anthracis*", Journal of Biological Chemistry 2003, 278(52): 52425-52431.
Muto, et al., "The guanine and cytosine content of genomic DNA and bacterial evolution", PNAS 1987, 84: 166-169.
Park, et al., "Optimized production and purification of *Bacillus anthracis* lethal factor", Protein Expr Purif 2000, 18(3): 293-302 (Abstract Only).
Sambrook, et al., "Molecular Cloning: A Laboratory Manual (2nd)", Sections 1.36-1.37, 1.53-1.59, 1.82-1.84, 15.14-15.18, 15.36-15.39, 15.44-15.48, and 15.49-15.53 1989.
Sharp, et al., "Codon usage patterns in *Escherichia coli, Bacillus subtilis, Saccharomyces cerevisiae, Schizosaccharomyces pombe, Drosophila melanogaster* and *Homo sapiens*; a review of the considerable within-species diversity", Nucleic Acids Research 1988, 16(17): 8207-8211.
Alvarez-Dominguez, et al., "The contribution of both oxygen and nitrogen intermediates to the intracellular killing mechanisms of C1q-opsonized *Listeria monocytogenes* by the macrophage-like IC-21 cell line," Immunology, 101:83-89 (2000).
Baillie, et al., "The expression of the protective antigen of *Bacillus anthracis* in *Bacillus subtilis*," Journal of Applied Microbiology, 84:741-746 (1998).
Baillie, et al., "Development of a *Bacillus subtilis* based system for the expression of the protective antigen of *Bacillus anthracis,*" Salisbury Medical Bulletin, Special Supplement No. 87, In Proceedings of the International Workshop on Anthrax, 133-135 (1995).
Baillie, et al., "Evaluation of *Bacillus subtilis* strain IS53 for the production of *Bacillus anthracis* protective antigen," Letters of Applied Microbiology, 19:225-227 (1994).

(Continued)

*Primary Examiner* — Robert A Zeman
(74) *Attorney, Agent, or Firm* — Kilpatrick Stockton & Townsend LLP

(57) ABSTRACT

An immunogenic reagent which produces an immune response which is protective against *Bacillus anthracis*, said reagent comprising one or more polypeptides which together represent up to three domains of the full length Protective Antigen (PA) of *B. anthracis* or variants of these, and at least one of said domains comprises domain 1 or domain 4 of PA or a variant thereof. The polypeptides of the immunogenic reagent as well as full length PA are produced by expression from *E. coli*. High yields of polypeptide are obtained using this method. Cells, vectors and nucleic acids used in the method are also described and claimed.

20 Claims, 10 Drawing Sheets

OTHER PUBLICATIONS

Belton, et al., "Studies on a Protective Antigen Produced In-Vitro from *Bacillus anthracis*: Medium and Methods of Production," Microbiological Research Department, Ministry of Supply, Porton, Wiltshire, 144-152 (1953).

Boslego, et al., *Vaccines and Immunotherapy*, Chapter 17 (1991).

Brossier, et al., "Functional Analysis of the Carboxy-Terminal Domain of *Bacillus anthracis* Protective Antigen," *Infection and Immunity*, 67(2):964-967 (1999).

Brossier, et al., "Role of Toxin Functional Domains in Anthrax Pathogenesis," *Infection and Immunity*, 68(4):1781-1786 (2000).

Cohen, et al., "Attenuated Nontoxinogenic and Nonencapsulated Recombinant *Bacillus anthracis* Spore Vaccines Protect against Anthrax," *Infection and Immunity*, 68(8):4549-4558 (2000).

Coulson, et al., "*Bacillus anthracis* protective antigen, expressed in *Salmonella typhimurium* SL 3261, affords protection against anthrax spore challenge," *Vaccine*, 12(5):1395-1401 (1994).

Thomas E. Creighton, *Proteins: Structures and Molecular Properties*, p. 315 (1984).

Thomas E. Creighton, *Protein Structure: A Practical Approach*, pp. 184-186 (1989).

Driks, "*Bacillus subtilis* Spore Coat," *Microbiology and Molecular Biology Reviews*, 63(1):1-20 (1999).

Ellis, *Vaccines*, W. B. Saunders Company, Chapter 29, pp. 568-574 (1988).

Escuyer, et al., "Anthrax Protective Antigen Interacts with a Specific Receptor on the Surface of CHO-K1 Cells," *Infection and Immunity*, 59(10):3381-3386 (1991).

Ezzell, et al., "Immunoelectrophoretic Analysis, Toxicity, and Kinetics of In Vitro Production of the Protective Antigen and Lethal Factor Components of *Bacillus anthracis* Toxin," *Infection and Immunity*, 45(3):761-767 (1984).

Friedlander, et al., "Macrophages Are Sensitive to Anthrax Lethal Toxin through an Acid-dependent Process," *The Journal of Biological Chemistry*, 261(16):7123-7126 (1986).

Greenspan, et al., *Nature Biotechnology*, 7:936-937 (1999).

Hambleton, et al., "Anthrax: the disease in relation to vaccines," *Vaccine*, 2:125-132 (1984).

Hoch, "51. spo0 Genes, the Phosphorelay, and the Initiation of Sporulation," *American Society for Microbiology*, Washington, D.C. 51:747-755, 1993.

Iacono-Connors, et al., "Expression of the *Bacillus anthracis* Protective Antigen Gene by Baculovirus and Vaccinia Virus Recombinants," *Infection and Immunity*, 58(2):366-372 (1990).

Ivins, et al., "Cloning and Expression of the *Bacillus anthracis* Protective Antigen Gene in *Bacillus subtilis*," *Infection and Immunity*, 54(2):537-542 (1986).

Klimpel, et al., "Anthrax toxin protective antigen is activated by a cell surface protease with the sequence specificity and catalytic properties of furin," *Proc. Natl. Acad. Sci. USA*, 89:10277-10281 (1992).

Lipman, et al., "Rapid and Sensitive Protein Similarity Searches," *Science*, 227:1435-1441 (1985).

Little, et al., "Characterization of lethal factor binding and cell receptor binding domains of protective antigen of *Bacillus anthracis* using monoclonal antibodies," *Microbiology*, 142:707-715 (1996).

Little, et al., "Comparative Efficacy of *Bacillus anthracis* Live Spore Vaccine and Protective Antigen Vaccine against Anthrax in the Guinea Pig," *Infection and Immunity*, 52(2):509-512 (1986).

Losick, et al., "Genetics of Endospore Formation in *Bacillus subtilis*," *Ann. Rev. Genet.*, 20:625-669 (1986).

McBride, et al., "Protective efficacy of a recombinant protective antigen against *Bacillus anthracis* challenge and assessment of immunological markers," *Vaccine*, 16(8):810-817 (1998).

Miller, et al., "Production and purification of recombinant protective antigen and protective efficacy against *Bacillus anthracis*," *Letters in Applied Microbiology*, 26:56-60 (1998).

Milne, et al., "Anthrax Protective Antigen Forms Oligomers during Intoxication of Mammalian Cells," *The Journal of Biological Chemistry*, 269(32):20607-20612 (1994).

Mogridge, et al., "Involvement of Domain 3 in Oligomerization by the Protective Antigen Moiety of Anthrax Toxin," *Journal of Bacteriology*, 183(6):2111-2116 (2001).

Nosoh, et al., *Protein Stability and Stabilization through Protein Engineering*, Chapter 7, p. 197, second paragraph (1991).

Oh, et al., Expression and Secretion of *Bacillus anthracis* Protective Antigen in *Bacillus brevis*, *Abstracts of the 3rd International Conference on Anthrax* (1998).

Petosa, et al., "Crystal structure of the anthrax toxin protective antigen," *Letters to Nature*, 385:833-938 (1997).

Quinn, et al., "Anthrax," Chapter 40, Topley and Wilsons *Microbiology and Microbial Infections*, Arnol, London, 799-818 (1998).

Sharma, et al., "Expression and Purification of Anthrax Toxin Protective Antigen from *Escherichia coli*," *Protein Expression and Purification*, 7:33-38 (1996).

Singh, et al., "Internalization and Processing of *Bacillus anthracis* Lethal Toxin by Toxin-sensitive and -resistant Cells," *The Journal of Biological Chemistry*, 264(19):11099-11102 (1989).

Singh, et al., Infection and Immunity, pp. 1853-1859 (Apr. 1999).

Turnbull, et al., "Development of Antibodies to Protective Antigen and Lethal Factor Components of Anthrax Toxin in Humans and Guinea Pigs and Their Relevance to Protective Immunity," *Infection and Immunity*, 52(2):356-363 (1986).

Turnbull, "Anthrax vaccines: past, present and future," *Vaccine*, 9:533-538 (1991).

Varughese, et al., "Identification of a Receptor-Binding Region within Domain 4 of the Protective Antigen Component of Anthrax Toxin," *Infection and Immunity*, 67(4):1860-1865 (1999).

Vodkin, et al., "Cloning of the Protective Antigen Gene of *Bacillus anthracis*," *Cell*, 34:693-697 (1983).

Welkos, et al., "Differences in Susceptibility of Inbred Mice to *Bacillus anthracis*," Infection and Immunity, 51(3):795-800 (1986).

Welkos, et al., "Sequence and analysis of the DNA encoding protective antigen of *Bacillus anthracis*," *Gene*, 69:287-300 (1988).

Willhite, et al., "Soluble Expression and One-Step Purification of Recombinant *Bacillus anthracis* Protective Antigen," *Protein and Peptide Letters*, 5(5):273-278 (1998).

Wu, et al., "Engineering a *Bacillus subtilis* Expression-Secretion System with a Strain Deficient in Six Extracellular Proteases," *Journal of Bacteriology*, 173(16):4952-4958 (1991).

\* cited by examiner

*Escherichia coli* [gbbct]: 14457 CDS's (4541860 codons)

Fields: [triplet] [frequency: per thousand] ([number])

```
UUU 22.0(100128)   UCU  9.3( 42367)   UAU 16.7( 75774)   UGU  5.2( 23461)
UUC 16.5( 74885)   UCC  8.9( 40365)   UAC 12.3( 55847)   UGC  6.3( 28747)
UUA 13.8( 62823)   UCA  7.9( 35837)   UAA  2.0(  9006)   UGA  1.0(  4428)
UUG 13.3( 60322)   UCG  8.7( 39546)   UAG  0.3(  1172)   UGG 14.5( 65630)

CUU 11.3( 51442)   CCU  7.2( 32678)   CAU 12.7( 57585)   CGU 20.7( 93997)
CUC 10.6( 48147)   CCC  5.4( 24383)   CAC  9.6( 43743)   CGC 21.1( 96053)
CUA  4.0( 18067)   CCA  8.5( 38663)   CAA 14.8( 67129)   CGA  3.7( 16607)
CUG 50.9(231373)   CCG 22.3(101467)   CAG 28.8(130898)   CGG  5.7( 25751)

AUU 29.9(135873)   ACU  9.5( 43256)   AAU 18.7( 84846)   AGU  9.1( 41544)
AUC 24.6(111878)   ACC 22.7(103121)   AAC 21.6( 98018)   AGC 15.6( 70867)
AUA  5.3( 24233)   ACA  7.9( 35995)   AAA 34.4(156169)   AGA  2.7( 12345)
AUG 27.2(123604)   ACG 14.0( 63696)   AAG 11.4( 51685)   AGG  1.6(  7423)

GUU 19.1( 86572)   GCU 16.2( 73677)   GAU 32.3(146794)   GGU 25.1(114185)
GUC 14.8( 67356)   GCC 25.0(113412)   GAC 19.3( 87759)   GGC 28.6(130043)
GUA 11.2( 51020)   GCA 20.6( 93390)   GAA 39.5(179460)   GGA  8.6( 39036)
GUG 25.5(115687)   GCG 32.2(146264)   GAG 18.5( 83804)   GGG 11.1( 50527)
```

Coding GC 51.37%  1st letter GC 58.50%  2nd letter GC 40.70%  3rd letter GC 54.90%

*Bacillus anthracis* [gbbct]: 180 CDS's (52031 codons)

Fields: [triplet] [frequency: per thousand] ([number])

```
UUU 33.5(  1745)   UCU 17.3(   902)   UAU 34.4(  1792)   UGU  6.1(   319)
UUC 10.2(   530)   UCC  5.3(   275)   UAC  9.4(   490)   UGC  2.1(   107)
UUA 44.2(  2301)   UCA 14.0(   730)   UAA  2.3(   118)   UGA  0.5(    24)
UUG 11.3(   589)   UCG  3.6(   188)   UAG  0.7(    37)   UGG  9.8(   511)

CUU 14.7(   763)   CCU 10.1(   525)   CAU 16.8(   873)   CGU 10.9(   567)
CUC  3.7(   195)   CCC  2.7(   141)   CAC  4.6(   239)   CGC  2.6(   137)
CUA 13.2(   686)   CCA 14.9(   773)   CAA 33.7(  1752)   CGA  6.8(   353)
CUG  4.7(   242)   CCG  4.6(   237)   CAG 10.4(   542)   CGG  1.8(    95)

AUU 44.6(  2322)   ACU 14.6(   761)   AAU 44.6(  2321)   AGU 16.5(   861)
AUC 11.8(   616)   ACC  5.2(   269)   AAC 13.7(   711)   AGC  5.1(   266)
AUA 24.9(  1295)   ACA 25.9(  1350)   AAA 69.5(  3614)   AGA 13.8(   720)
AUG 23.8(  1240)   ACG  8.1(   419)   AAG 23.5(  1223)   AGG  4.3(   226)

GUU 19.9(  1036)   GCU 17.9(   930)   GAU 39.7(  2068)   GGU 17.3(   900)
GUC  5.2(   268)   GCC  4.7(   244)   GAC  8.8(   456)   GGC  5.4(   279)
GUA 26.8(  1395)   GCA 22.6(  1178)   GAA 55.7(  2897)   GGA 20.2(  1049)
GUG  9.7(   507)   GCG  7.1(   368)   GAG 19.3(  1003)   GGG  8.9(   461)
```

Coding GC 33.59%  1st letter GC 44.51%  2nd letter GC 31.07%  3rd letter GC 25.20%

Figure 1

```
   1 AAGCTTCATA TGGAAGTAAA GCAAGAGAAC CGTCTGCTGA ACGAATCTGA ATCCAGCTCT
  61 CAGGGCCTGC TTGGTTACTA TTTCTCTGAC CTGAACTTCC AAGCACCGAT GGTTGTAACC
 121 AGCTCTACCA CTGGCGATCT GTCCATCCCG TCTAGTGAAC TTGAGAACAT TCCAAGCGAG
 181 AACCAGTATT TCCAGTCTGC AATCTGGTCC GGTTTTATCA AAGTCAAGAA ATCTGATGAA
 241 TACACGTTTG CCACCTCTGC TGATAACCAC GTAACCATGT GGGTTGACGA TCAGGAAGTG
 301 ATCAACAAAG CATCCAACTC CAACAAAATT CGTCTGGAAA AAGGCCGTCT GTATCAGATC
 361 AAGATTCAGT ACCAACGCGA GAACCCGACT GAAAAGGCC TGGACTTTAA ACTGTATTGG
 421 ACTGATTCTC AGAACAAGAA AGAAGTGATC AGCTCTGACA ATCTGCAACT GCCGGAATTG
 481 AAACAGAAAA GCTCCAACTC TCGTAAGAAA CGTTCCACCA GCGCTGGCCC GACCGTACCA
 541 GATCGCGACA ACGATGGTAT TCCGGACTCT CTGGAAGTTG AAGGCTACAC GGTTGATGTA
 601 AAGAACAAAC GTACCTTCCT TAGTCCGTGG ATCTCCAATA TTCACGAGAA GAAAGGTCTG
 661 ACCAAATACA AATCCAGTCC GGAAAAATGG TCCACTGCAT CTGATCCGTA CTCTGACTTT
 721 GAGAAAGTGA CCGGTCGTAT CGACAAGAAC GTCTCTCCGG AAGCACGCCA TCCACTGGTT
 781 GCTGCGTATC CGATCGTACA TGTTGACATG GAAAACATCA TTTTGTCCAA GAACGAAGAC
 841 CAGTCCACTC AGAACACTGA CTCTGAAACT CGTACCATCT CCAAGAACAC CTCCACGTCT
 901 CGTACTCACA CCAGTGAAGT ACATGGTAAC GCTGAAGTAC ACGCCTCTTT CTTTGACATC
 961 GGCGGCTCTG TTAGCGCTGG CTTCTCCAAC TCTAATTCTT CTACTGTTGC CATTGATCAC
1021 TCTCTGAGTC TGGCTGGCGA ACGTACCTGG GCAGAGACCA TGGGTCTTAA CACTGCTGAT
1081 ACCGCGCGTC TGAATGCTAA CATTCGCTAC GTCAACACTG GTACGGCACC GATCTACAAC
1141 GTACTGCCAA CCACCAGCCT GGTTCTGGGT AAGAACCAGA CTCTTGCGAC CATCAAAGCC
1201 AAAGAGAACC AACTGTCTCA GATTCTGGCA CCGAATAACT ACTATCCTTC CAAGAACCTG
1261 GCTCCGATCG CACTGAACGC ACAGGATGAC TTCTCTTCCA CTCCGATCAC CATGAACTAC
1321 AACCAGTTCC TGGAACTTGA GAAGACCAAA CAGCTGCGTC TTGACACTGA CCAAGTGTAC
1381 GGTAACATCG CGACCTACAA CTTTGAGAAC GGTCGCGTCC GCGTTGACAC AGGCTCTAAT
1441 TGGTCTGAAG TACTGCCTCA GATTCAGGAA ACCACCGCTC GTATCATCTT CAACGGTAAA
1501 GACCTGAACC TGGTTGAACG TCGTATTGCT GCTGTGAACC CGTCTGATCC ATTAGAGACC
1561 ACCAAACCGG ATATGACTCT GAAAGAAGCC CTGAAGATCG CCTTTGGCTT CAACGAGCCG
1621 AACGGTAATC TTCAGTACCA AGGTAAAGAC ATCACTGAAT TGACTTCAA CTTTGATCAG
1681 CAGACCTCTC AGAATATCAA GAACCAACTG GCTGAGCTGA ACGCGACCAA TATCTATACG
1741 GTACTCGACA AGATCAAACT GAACGCGAAA ATGAACATTC TGATTCGCGA CAAACGTTTC
1801 CACTACGATC GTAATAACAT CGCTGTTGGC GCTGATGAAT CTGTTGTGAA AGAAGCGCAT
1861 CGCGAAGTCA TCAACTCCAG CACCGAAGGC TGCTTCTGA ACATCGACAA AGACATTCGT
1921 AAGATCCTGT CTGGTTACAT TGTTGAGATC GAAGACACCG AAGGCCTGAA AGAAGTGATC
1981 AATGATCGTT ACGACATGCT GAACATCAGC TCTCTGCGTC AAGATGGTAA GACGTTCATT
2041 GACTTCAAGA AATACAACGA CAAACTTCCG CTGTATATCT CTAATCCGAA CTACAAAGTG
2101 AACGTTTACG CTGTTACCAA AGAGAACACC ATCATCAATC CATCTGAGAA CGGCGATACC
2161 TCTACCAACG GTATCAAGAA GATTCTGATC TTCTCCAAGA AAGGTTACGA GATCGGTTAA
2221 TAGGATCC
```

(SEQ ID No 1)

Figure 2

```
  1 EVKQENRLLN ESESSSQGLL GYYFSDLNFQ APMVVTSSTT GDLSIPSSEL ENIPSENQYF
 61 QSAIWSGFIK VKKSDEYTFA TSADNHVTMW VDDQEVINKA SNSNKIRLEK GRLYQIKIQY
121 QRENPTEKGL DFKLYWTDSQ NKKEVISSDN LQLPELKQKS SNSRKKRSTS AGPTVPDRDN
181 DGIPDSLEVE GYTVDVKNKR TFLSPWISNI HEKKGLTKYK SSPEKWSTAS DPYSDFEKVT
241 GRIDKNVSPE ARHPLVAA
```

(Seq ID No 3)

```
  1 gaagttaaac aggagaaccg ttattaaat  gaatcagaat caagttccca ggggttacta
 61 ggatactatt ttagtgattt gaattttcaa gcacccatgg tggttacctc ttctactaca
121 ggggatttat ctattcctag ttctgagtta gaaaatattc catcggaaaa ccaatatttt
181 caatctgcta tttggtcagg atttatcaaa gttaagaaga gtgatgaata tacatttgct
241 acttccgctg ataatcatgt aacaatgtgg gtagatgacc aagaagtgat taataaagct
301 tctaattcta acaaaatcag attagaaaaa ggaagattat atcaaataaa aattcaatat
361 caacgagaaa atcctactga aaaggattg  gatttcaagt tgtactggac cgattctcaa
421 aataaaaaag aagtgatttc tagtgataac ttacaattgc cagaattaaa acaaaaatct
481 tcgaactcaa gaaaaaagcg aagtacaagt gctggaccta cggttccaga ccgtgacaat
541 gatggaatcc ctgattcatt agaggtagaa ggatatacgg ttgatgtcaa aaataaaaga
601 acttttcttt caccatggat ttctaatatt catgaaaaga aaggattaac caaatataaa
661 tcatctcctg aaaaatggag cacggcttct gatccgtaca gtgatttcga aaaggttaca
721 ggacggattg ataagaatgt atcaccagag gcaagacacc cccttgtggc agct
```

(Seq ID No 4)

```
  1 EVKQENRLLN ESESSSQGLL GYYFSDLNFQ APMVVTSSTT GDLSIPSSEL ENIPSENQYF
 61 QSAIWSGFIK VKKSDEYTFA TSADNHVTMW VDDQEVINKA SNSNKIRLEK GRLYQIKIQY
121 QRENPTEKGL DFKLYWTDSQ NKKEVISSDN LQLPELKQKS SNSRKKRSTS AGPTVPDRDN
181 DGIPDSLEVE GYTVDVKNKR TFLSPWISNI HEKKGLTKYK SSPEKWSTAS DPYSDFEKVT
241 GRIDKNVSPE ARHPLVAAYP IVHVDMENII LSKNEDQSTQ NTDSETRTIS KNTSTSRTHT
301 SEVHGNAEVH ASFFDIGGSV SAGFSNSNSS TVAIDHSLSL AGERTWAETM GLNTADTARL
361 NANIRYVNTG TAPIYNVLPT TSLVLGKNQT LATIKAKENQ LSQILAPNNY YPSKNLAPIA
421 LNAQDDFSST PITMNYNQFL ELEKTKQLRL DTDQVYGNIA TYNFENGRVR VDTGSNWSEV
481 LPQIQET
```

(SEQ ID No 5)

Figure 3

```
   1 gaagttaaac aggagaaccg gttattaaat gaatcagaat caagttccca ggggttacta
  61 ggatactatt ttagtgattt gaattttcaa gcacccatgg tggttacttc ttctactaca
 121 ggggatttat ctattcctag ttctgagtta gaaaatattc catcggaaaa ccaatatttt
 181 caatctgcta tttggtcagg atttatcaaa gttaagaaga gtgatgaata tacatttgct
 241 acttccgctg ataatcatgt aacaatgtgg gtagatgacc aagaagtgat taataaagct
 301 tctaattcta acaaaatcag attagaaaaa ggaagattat atcaaataaa aattcaatat
 361 caacgagaaa atcctactga aaaaggattg gatttcaagt tgtactggac cgattctcaa
 421 aataaaaaag aagtgatttc tagtgataac ttacaactgc cagaattaaa acaaaaatct
 481 tcgaactcaa gaaaaaagcg aagtacaagt gctggaccta cggttccaga ccgtgacaat
 541 gatggaatcc ctgattcatt agaggtagaa ggatatacgg ttgatgtcaa aaataaaga
 601 acttttcttt caccatggat ttctaatatt catgaaaaga aaggattaac caatatataa
 661 tcatctcctg aaaaatggag cacggcttct gatccgtaca gtgatttcga aaaggttaca
 721 ggacggattg ataagaatgt atcaccagag gcaagacacc cccttgtggc agcttatccg
 781 attgtacatg tagatatgga gaatattat ctctcaaaaa atgaggatca atccacacag
 841 aatactgata gtgaaacgag aacaataagt aaaaatactt ctacaagtag gacacatact
 901 agtgaagtac atggaaatgc agaagtgcat gcgtcgttct tgatattgg tgggagtgta
 961 tctgcaggat ttagtaattc gaattcaagt acggtcgcaa ttgatcattc actatctcta
1021 gcagggggaaa gaacttgggc tgaaacaatg ggtttaaata ccgctgatac agcaagatta
1081 aatgccaata ttagatatgt aaatactggg acggctccaa tctacaacgt gttaccaacg
1141 acttcgttag tgttaggaaa aaatcaaaca ctcgcgacaa ttaaagctaa ggaaaaccaa
1201 ttaagtcaaa tacttgcacc taataattat tatccttcta aaaacttggc gccaatcgca
1261 ttaaatgcac aagacgattt cagttctact ccaattacaa tgaattacaa tcaatttctt
1321 gagttagaaa aaacgaaaca attaagatta gatacggatc aagtatatgg gaatatagca
1381 acatacaatt tgaaaatgg aagagtgagg gtggatacag gctcgaactg gagtgaagtg
1441 ttaccgcaaa ttcaagaaac a
```

(SEQ ID No 6)

```
  1 SAGPTVPDRD NDGIPDSLEV EGYTVDVKNK RTFLSPWISN IHEKKGLTKY KSSPEKWSTA
 61 SDPYSDFEKV TGRIDKNVSP EARHPLVAAY PIVHVDMENI ILSKNEDQST QNTDSETRTI
121 SKNTSTSRTH TSEVHGNAEV HASFFDIGGS VSAGFSNSNS STVAIDHSLS LAGERTWAET
181 MGLNTADTAR LNANIRYVNT GTAPIYNVLP TTSLVLGKNQ TLATIKAKEN QLSQILAPNN
241 YYPSKNLAPI ALNAQDDFSS TPITMNYNQF LELEKTKQLR LDTDQVYGNI ATYNFENGRV
301 RVDTGSNWSE VLPQIQET
```

(SEQ ID No 7)

Figure 3 Cont.

```
  1 agtgctggac ctacggttcc agaccgtgac aatgatggaa tccctgattc attagaggta
 61 gaaggatata cggttgatgt caaaaataaa agaactttc tttcaccatg gatttctaat
121 attcatgaaa agaaaggatt aaccaaatat aaatcatctc ctgaaaaatg gagcacggct
181 tctgatccgt acagtgattt cgaaaaggtt acaggacgga ttgataagaa tgtatcacca
241 gaggcaagac accccttgt ggcagcttat ccgattgtac atgtagatat ggagaatatt
301 attctctcaa aaaatgagga tcaatccaca cagaatactg atagtgaaac gagaacaata
361 agtaaaaata cttctacaag taggacacat actagtgaag tacatggaaa tgcagaagtg
421 catgcgtcgt tctttgatat tggtgggagt gtatctgcag gatttagtaa ttcgaattca
481 agtacggtcg caattgatca ttcactatct ctagcagggg aaagaacttg gctgaaaca
541 atgggtttaa ataccgctga tacagcaaga ttaaatgcca atattagata tgtaaatact
601 gggacggctc caatctacaa cgtgttacca acgacttcgt tagtgttagg aaaaaatcaa
661 acactcgcga caattaaagc taaggaaaac caattaagtc aaatacttgc acctaataat
721 tattatcctt ctaaaaactt ggcgccaatc gcattaaatg cacaagacga tttcagttct
781 actccaatta caatgaatta caatcaattt cttgagttag aaaaaacgaa acaattaaga
841 ttagatacgg atcaagtata tgggaatata gcaacataca ttttgaaaa tggaagagtg
901 agggtggata caggctcgaa ctggagtgaa gtgttaccgc aaattcaaga aaca
```

(SEQ ID No 8)

```
  1 SAGPTVPDRD NDGIPDSLEV EGYTVDVKNK RTFLSPWISN IHEKKGLTKY KSSPEKWSTA
 61 SDPYSDFEKV TGRIDKNVSP EARHPLVAAY PIVHVDMENI ILSKNEDQST QNTDSETRTI
121 SKNTSTSRTH TSEVHGNAEV HASFFDIGGS VSAGFSNSNS STVAIDHSLS LAGERTWAET
181 MGLNTADTAR LNANIRYVNT GTAPIYNVLP TTSLVLGKNQ TLATIKAKEN QLSQILAPNN
241 YYPSKNLAPI ALNAQDDFSS TPITMNYNQF LELEKTKQLR LDTDQVYGNI ATYNFENGRV
301 RVDTGSNWSE VLPQIQETTA RIIFNGKDLN LVERRIAAVN PSDPLETTKP DMTLKEALKI
361 AFGFNEPNGN LQYQGKDITE FDFNFDQQTS QNIKNQLAEL NATNIYTVLD KIKLNAKMNI
421 LIRDKR
```

(SEQ ID No 9)

Figure 3. Cont.

```
   1 agtgctggac ctacggttcc agaccgtgac aatgatggaa tccctgattc attagaggta
  61 gaaggatata cggttgatgt caaaaataaa agaacttttc tttcaccatg gatttctaat
 121 attcatgaaa agaaaggatt aaccaaatat aaatcatctc ctgaaaaatg gagcacggct
 181 tctgatccgt acagtgattt cgaaaaggtt acaggacgga ttgataagaa tgtatcacca
 241 gaggcaagac accccttgt ggcagcttat ccgattgtac atgtagatat ggagaatatt
 301 attctctcaa aaaatgagga tcaatccaca cagaatactg atagtgaaac gagaacaata
 361 agtaaaaata cttctacaag taggacacat actagtgaag tacatggaaa tgcagaagtg
 421 catgcgtcgt tctttgatat tggtgggagt gtatctgcag gatttagtaa ttcgaattca
 481 agtacggtcg caattgatca ttcactatct ctagcagggg aaagaacttg ggctgaaaca
 541 atgggtttaa ataccgctga tacagcaaga ttaaatgcca atattagata tgtaaatact
 601 gggacggctc caatctacaa cgtgttacca acgacttcgt tagtgttagg aaaaaatcaa
 661 acactcgcga caattaaagc taaggaaaac caattaagtc aaatacttgc acctaataat
 721 tattatcctt ctaaaaactt ggcgccaatc gcattaaatg cacaagacga tttcagttct
 781 actccaatta caatgaatta caatcaattt cttgagttag aaaaaacgaa acaattaaga
 841 ttagatacgg atcaagtata tgggaatata gcaacataca attttgaaaa tggaagagtg
 901 agggtggata caggctcgaa ctggagtgaa gtgttaccgc aaattcaaga aacaactgca
 961 cgtatcattt taatgaaaa agatttaaat ctggtagaaa ggcggatagc ggcggttaat
1021 cctagtgatc cattagaaac gactaaaccg gatatgacat taaaagaagc ccttaaaata
1081 gcatttggat ttaacgaacc gaatggaaac ttacaatatc aagggaaaga cataaccgaa
1141 tttgatttta atttcgatca acaaacatct caaaatatca agaatcagtt agcggaatta
1201 aacgcaacta acatatatac tgtattagat aaaatcaaat taaatgcaaa aatgaatatt
1261 ttaataagag ataaacgt
```

(SEQ ID No 10)

```
  1 EVKQENRLLN ESESSSQGLL GYYFSDLNFQ APMVVTSSTT GDLSIPSSEL ENIPSENQYF
 61 QSAIWSGFIK VKKSDEYTFA TSADNHVTMW VDDQEVINKA SNSNKIRLEK GRLYQIKIQY
121 QRENPTEKGL DFKLYWTDSQ NKKEVISSDN LQLPELKQKS SNSRKKRSTS AGPTVPDRDN
181 DGIPDSLEVE GYTVDVKNKR TFLSPWISNI HEKKGLTKYK SSPEKWSTAS DPYSDFEKVT
241 GRIDKNVSPE ARHPLVAAYP IVHVDMENII LSKNEDQSTQ NTDSETRTIS KNTSTSRTHT
301 SEVHGNAEVH ASFFDIGGSV SAGFSNSNSS TVAIDHSLSL AGERTWAETM GLNTADTARL
361 NANIRYVNTG TAPIYNVLPT TSLVLGKNQT LATIKAKENQ LSQILAPNNY YPSKNLAPIA
421 LNAQDDFSST PITMNYNQFL ELEKTKQLRL DTDQVYGNIA TYNFENGRVR VDTGSNWSEV
481 LPQIQETTAR IIFNGKDLNL VERRIAAVNP SDPLETTKPD MTLKEALKIA FGFNEPNGNL
541 QYQGKDITEF DFNFDQQTSQ NIKNQLAELN ATNIYTVLDK IKLNAKMNIL IRDKR
```

(SEQ ID No 11)

Figure 3 Cont.

```
   1 gaagttaaac aggagaaccg gttattaaat gaatcagaat caagttccca ggggttacta
  61 ggatactatt ttagtgattt gaattttcaa gcacccatgg tggttacctc ttctactaca
 121 ggggatttat ctattcctag ttctgagtta gaaaatattc catcggaaaa ccaatatttt
 181 caatctgcta tttggtcagg atttatcaaa gttaagaaga gtgatgaata tacatttgct
 241 acttccgctg ataatcatgt aacaatgtgg gtagatgacc aagaagtgat taataaagct
 301 tctaattcta acaaaatcag attagaaaaa ggaagattat atcaaataaa aattcaatat
 361 caacgagaaa atcctactga aaaaggattg gatttcaagt tgtactggac cgattctcaa
 421 aataaaaaag aagtgatttc tagtgataac ttacaattgc cagaattaaa acaaaaatct
 481 tcgaactcaa gaaaaaagcg aagtacaagt gctggaccta cggttccaga ccgtgacaat
 541 gatggaatcc ctgattcatt agaggtagaa ggatatacgg ttgatgtcaa aaataaaaga
 601 actttctttt caccatggat ttctaatatt catgaaaaga aaggattaac caaatataaa
 661 tcatctcctg aaaaatggag cacggcttct gatccgtaca gtgatttcga aaaggttaca
 721 ggacggattg ataagaatgt ataccagag gcaagacacc cccttgtggc agcttatccg
 781 attgtacatg tagatatgga gaatattatt ctctcaaaaa atgaggatca atccacacag
 841 aatactgata gtgaaacgag aacaataagt aaaaatactt ctacaagtag gacacatact
 901 agtgaagtac atggaaatgc agaagtgcat gcgtcgttct ttgatattgg tgggagtgta
 961 tctgcaggat ttagtaattc gaattcaagt acggtcgcaa ttgatcattc actatctcta
1021 gcaggggaaa gaacttgggc tgaaacaatg ggtttaaata ccgctgatac agcaagatta
1081 aatgccaata ttagatatgt aaatactggg acggctccaa tctacaacgt gttaccaacg
1141 acttcgttag tgttaggaaa aaatcaaaca ctcgcgacaa ttaaagctaa ggaaaaccaa
1201 ttaagtcaaa tacttgcacc taataattat tatccttcta aaaacttggc gccaatcgca
1261 ttaaatgcac aagacgattt cagttctact ccaattacaa tgaattacaa tcaatttctt
1321 gagttagaaa aacgaaaca attaagatta gatacggatc aagtatatgg gaatatagca
1381 acatacaatt tgaaaatgg aagagtgagg gtggatacag gctcgaactg gagtgaagtg
1441 ttaccgcaaa ttcaagaaac aactgcacgt atcattttta tggaaaaga tttaaatctg
1501 gtagaaaggc ggatagcggc ggttaatcct agtgatccat agaaacgac taaaccggat
1561 atgacattaa agaagcccct taaatagca tttggattta acgaaccgaa tggaaactta
1621 caatatcaag ggaaagacat aaccgaattt gattttaatt tcgatcaaca acatctcaa
1681 aatatcaaga atcagttagc ggaattaaac gcaactaaca tatatactgt attagataaa
1741 atcaaattaa atgcaaaaat gaatatttta ataagagata aacgt
```

(SEQ ID No 12)

```
  1 EVKQENRLLN ESESSSQGLL GYYFSDLNFQ APMVVTSSTT GDLSIPSSEL ENIPSENQYF
 61 QSAIWSGFIK VKKSDEYTFA TSADNHVTMW VDDQEVINKA SNSNKIRLEK GRLYQIKIQY
121 QRENPTEKGL DFKLYWTDSQ NKKEVISSDN LQLPELKQKS SNSRKKRSTS AGPTVPDRDN
181 DGIPDSLEVE GYTVDVKNKR TFLSPWISNI HEKKGLTKYK SSPEKWSTAS DPYSDFEKVT
241 GRIDKNVSPE ARHPLVAAYP IVHVDMENII LSKNEDQSTQ NTDSQTRTIS KNTSTSRTHT
301 SEVHGNAEVH ASFFDIGGSV SAGFSNSNSS TVAIDHSLSL AGERTWAETM GLNTADTARL
361 NANIRYVNTG TAPIYNVLPT TSLVLGKNQT LATIKAKENQ LSQILAPNNY YPSKNLAPIA
421 LNAQDDFSST PITMNYNQFL ELEKTKQLRL DTDQVYGNIA TYNFENGRVR VDTGSNWSEV
481 LPQIQETTAR IIFNGKDLNL VERRIAAVNP SDPLETTKPD MTLKEALKIA FGFNEPNGNL
541 QYQGKDITEF DFNFDQQTSQ NIKNQLAELN ATNIYTVLDK IKLNAKMNIL IRDKRFHYDR
601 NNIAVGADES VVKEAHREVI NSSTEGLLLN IDKDIRKILS GYIVEIEDTE GLKEVINDRY
661 DMLNISSLRQ DGKTFIDFKK YNDKLPLYIS NPNYKVNVYA VTKENTIINP SENGDTSTNG
721 IKKILIFSKK GYEIG
```

(SEQ ID No 13)

Figure 3 Cont.

```
   1 gaagttaaac aggagaaccg gttattaaat gaatcagaat caagttccca ggggttacta
  61 ggatactatt ttagtgattt gaattttcaa gcacccatgg tggttacctc ttctactaca
 121 ggggatttat ctattcctag ttctgagtta gaaatattc catcggaaaa ccaatatttt
 181 caatctgcta tttggtcagg atttatcaaa gttaagaaga gtgatgaata tacatttgct
 241 acttccgctg ataatcatgt aacaatgtgg gtagatgacc aagaagtgat taataaagct
 301 tctaattcta acaaaatcag attagaaaaa ggaagattat atcaaataaa aattcaatat
 361 caacgagaaa atcctactga aaaggattg gatttcaagt tgtactggac cgattctcaa
 421 aataaaaaag aagtgatttc tagtgataac ttacaattgc cagaattaaa acaaaaatct
 481 tcgaactcaa gaaaaaagcg aagtacaagt gctggaccta cggttccaga ccgtgacaat
 541 gatggaatcc ctgattcatt agaggtagaa ggatatacgg ttgatgtcaa aaataaaaga
 601 actttctttt caccatggat ttctaatatt catgaaaaga aaggattaac caaatataaa
 661 tcatctcctg aaaaatggag cacggcttct gatccgtaca gtgatttcga aaaggttaca
 721 ggacggattg ataagaatgt atcaccagag gcaagacacc cccttgtggc agcttatccg
 781 attgtacatg tagatatgga gaatattatt ctctcaaaaa atgaggatca atccacacag
 841 aatactgata gtgaaacgag aacaataagt aaaaatactt ctacaagtag gacacatact
 901 agtgaagtac atggaaatgc agaagtgcat gcgtcgttct ttgatattgg tgggagtgta
 961 tctgcaggat ttagtaattc gaattcaagt acggtcgcaa ttgatcattc actatctcta
1021 gcaggggaaa gaacttgggc tgaaacaatg ggtttaaata ccgctgatac agcaagatta
1081 aatgccaata ttagatatgt aaatactggg acggctccaa tctacaacgt gttaccaacg
1141 acttcgttag tgttaggaaa aaatcaaaca ctcgcgacaa ttaaagctaa ggaaaaccaa
1201 ttaagtcaaa tacttgcacc taataattat tatccttcta aaaacttggc gccaatcgca
1261 ttaaatgcac aagacgattt cagttctact ccaattacaa tgaattacaa tcaatttctt
1321 gagttagaaa aaacgaaaca attaagatta gatacggatc aagtatatgg gaatatagca
1381 acatacaatt ttgaaaatgg aagagtgagg gtggatacag gctcgaactg gagtgaagtg
1441 ttaccgcaaa ttcaagaaac aactgcacgt atcattttta atggaaaaga tttaaatctg
1501 gtagaaaggc ggatagcggc ggttaatcct agtgatccat tagaaacgac taaccggat
1561 atgacattaa aagaagccct taaaatagca tttggattta acgaaccgaa tggaaactta
1621 caatatcaag ggaaagacat aaccgaattt gatttttaatt tcgatcaaca aacatctcaa
1681 aaatatcaaga atcagttagc ggaattaaac gcaactaaca tatatactgt attagataaa
1741 atcaaattaa atgcaaaaat gaatatttta ataagagata aacgttttca ttatgataga
1801 aataacatag cagttggggc ggatgagtca gtagttaagg aggctcatag agaagtaatt
1861 aattcgtcaa cagagggatt attgttaaat attgataagg atataagaaa aatattatca
1921 ggttatattg tagaaattga agatactgaa gggcttaaag aagttataaa tgacagatat
1981 gatatgttga atatttctag tttacggcaa gatggaaaaa catttataga ttttaaaaaa
2041 tataatgata aattaccgtt atatataagt aatcccaatt ataaggtaaa tgtatatgct
2101 gttactaaag aaaacactat tattaatcct agtgagaatg gggatactag taccaacggg
2161 atcaagaaaa ttttaatctt ttctaaaaaa ggctatgaga taggataa
```

(SEQ ID No 14)

Figure 3 Cont.

```
  1 FHYDRNNIAV GADESVVKEA HREVINSSTE GLLLNIDKDI RKILSGYIVE IEDTEGLKEV
 61 INDRYDMLNI SSLRQDGKTF IDFKKYNDKL PLYISNPNYK VNVYAVTKEN TIINPSENGD
121 TSTNGIKKIL IFSKKGYEIG
```

(SEQ ID No 15)

```
  1 tttcattatg atagaaataa catagcagtt ggggcggatg agtcagtagt taaggaggct
 61 catagagaag taattaattc gtcaacagag ggattattgt taaatattga taaggatata
121 agaaaaatat tatcaggtta tattgtagaa attgaagata ctgaagggct taaagaagtt
181 ataaatgaca gatatgatat gttgaatatt tctagtttac ggcaagatgg aaaaacattt
241 atagatttta aaaatataa tgataaatta ccgttatata taagtaatcc caattataag
301 gtaaatgtat atgctgttac taaagaaaac actattatta atcctagtga gaatggggat
361 actagtacca acgggatcaa gaaaatttta atcttttcta aaaaaggcta tgagatagga
421 taa
```

(SEQ ID No 16)

Figure 4

SEQUENCE LISTING

<160> NUMBER OF SEQ ID NOS: 16

<210> SEQ ID NO 1
<211> LENGTH: 2228
<212> TYPE: DNA
<213> ORGANISM: Artificial Sequence
<220> FEATURE:
<223> OTHER INFORMATION: Description of Artificial Sequence: Nucleic
      acid which encodes the protective antigen of Bacillus
      anthracis

<400> SEQUENCE: 1

```
aagcttcata tggaagtaaa gcaagagaac cgtctgctga acgaatctga atccagctct      60
cagggcctgc ttggttacta tttctctgac ctgaacttcc aagcaccgat ggttgtaacc     120
agctctacca ctggcgatct gtccatcccg tctagtgaac ttgagaacat tccaagcgag     180
aaccagtatt tccagtctgc aatctggtcc ggttttatca aagtcaagaa atctgatgaa     240
```

-continued

| | |
|---|---|
| tacacgtttg ccacctctgc tgataaccac gtaaccatgt gggttgacga tcaggaagtg | 300 |
| atcaacaaag catccaactc caacaaaatt cgtctggaaa aaggccgtct gtatcagatc | 360 |
| aagattcagt accaacgcga gaacccgact gaaaaaggcc tggactttaa actgtattgg | 420 |
| actgattctc agaacaagaa agaagtgatc agctctgaca atctgcaact gccggaattg | 480 |
| aaacagaaaa gctccaactc tcgtaagaaa cgttccacca gcgctggccc gaccgtacca | 540 |
| gatcgcgaca acgatggtat tccggactct ctggaagttg aaggctacac ggttgatgta | 600 |
| aagaacaaac gtaccttcct tagtccgtgg atctccaata ttcacgagaa gaaaggtctg | 660 |
| accaaataca aatccagtcc ggaaaaatgg tccactgcat ctgatccgta ctctgacttt | 720 |
| gagaaagtga ccggtcgtat cgacaagaac gtctctccgg aagcacgcca tccactggtt | 780 |
| gctgcgtatc cgatcgtaca tgttgacatg gaaaacatca ttttgtccaa gaacgaagac | 840 |
| cagtccactc agaacactga ctctgaaact cgtaccatct ccaagaacac ctccacgtct | 900 |
| cgtactcaca ccagtgaagt acatggtaac gctgaagtac acgcctcttt ctttgacatc | 960 |
| ggcggctctg ttagcgctgg cttctccaac tctaattctt ctactgttgc cattgatcac | 1020 |
| tctctgagtc tggctggcga acgtacctgg gcagagacca tgggtcttaa cactgctgat | 1080 |
| accgcgcgtc tgaatgctaa cattcgctac gtcaacactg gtacggcacc gatctacaac | 1140 |
| gtactgccaa ccaccagcct ggttctgggt aagaaccaga ctcttgcgac catcaaagcc | 1200 |
| aaagagaacc aactgtctca gattctggca ccgaataact actatccttc caagaacctg | 1260 |
| gctccgatcg cactgaacgc acaggatgac ttctcttcca ctccgatcac catgaactac | 1320 |
| aaccagttcc tggaacttga agaccaaaa cagctgcgtc ttgacactga ccaagtgtac | 1380 |
| ggtaacatcg cgacctacaa ctttgagaac ggtcgcgtcc gcgttgacac aggctctaat | 1440 |
| tggtctgaag tactgcctca gattcaggaa accaccgctc gtatcatctt caacggtaaa | 1500 |
| gacctgaacc tggttgaacg tcgtattgct gctgtgaacc cgtctgatcc attagagacc | 1560 |
| accaaaccgg atatgactct gaaagaagcc ctgaagatcg cctttggctt caacgagccg | 1620 |
| aacggtaatc ttcagtacca aggtaaagac atcactgaat ttgacttcaa ctttgatcag | 1680 |
| cagacctctc agaatatcaa gaaccaactg gctgagctga acgcgaccaa tatctatacg | 1740 |
| gtactcgaca agatcaaact gaacgcgaaa atgaacattc tgattcgcga caaacgtttc | 1800 |
| cactacgatc gtaataacat cgctgttggc gctgatgaat ctgttgtgaa agaagcgcat | 1860 |
| cgcgaagtca tcaactccag caccgaaggc ctgcttctga acatcgacaa agacattcgt | 1920 |
| aagatcctgt ctggttacat tgttgagatc gaagacaccg aaggcctgaa agaagtgatc | 1980 |
| aatgatcgtt acgacatgct gaacatcagc tctctgcgtc aagatggtaa gacgttcatt | 2040 |
| gacttcaaga aatacaacga caaacttccg ctgtatatct ctaatccgaa ctacaaagtg | 2100 |
| aacgtttacg ctgttaccaa agagaacacc atcatcaatc catctgagaa cggcgatacc | 2160 |
| tctaccaacg gtatcaagaa gattctgatc ttctccaaga aaggttacga gatcggttaa | 2220 |
| taggatcc | 2228 |

<210> SEQ ID NO 2
<211> LENGTH: 10
<212> TYPE: PRT
<213> ORGANISM: Bacillus anthracis

<400> SEQUENCE: 2

Met Glu Val Lys Gln Glu Asn Arg Leu Leu
1               5                   10

```
<210> SEQ ID NO 3
<211> LENGTH: 258
<212> TYPE: PRT
<213> ORGANISM: Bacillus anthracis

<400> SEQUENCE: 3

Glu Val Lys Gln Glu Asn Arg Leu Leu Asn Glu Ser Glu Ser Ser Ser
  1               5                  10                  15

Gln Gly Leu Leu Gly Tyr Tyr Phe Ser Asp Leu Asn Phe Gln Ala Pro
             20                  25                  30

Met Val Val Thr Ser Ser Thr Thr Gly Asp Leu Ser Ile Pro Ser Ser
         35                  40                  45

Glu Leu Glu Asn Ile Pro Ser Glu Asn Gln Tyr Phe Gln Ser Ala Ile
 50                  55                  60

Trp Ser Gly Phe Ile Lys Val Lys Lys Ser Asp Glu Tyr Thr Phe Ala
 65                  70                  75                  80

Thr Ser Ala Asp Asn His Val Thr Met Trp Val Asp Asp Gln Glu Val
                 85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala

<210> SEQ ID NO 4
<211> LENGTH: 774
<212> TYPE: DNA
<213> ORGANISM: Artificial Sequence
<220> FEATURE:
<223> OTHER INFORMATION: Description of Artificial Sequence: DNA
      sequence used to encode SEQ ID NO: 3

<400> SEQUENCE: 4
gaagttaaac aggagaaccg gttattaaat gaatcagaat caagttccca ggggttacta      60
ggatactatt ttagtgattt gaattttcaa gcacccatgg tggttacctc ttctactaca     120
ggggatttat ctattcctag ttctgagtta gaaaatattc catcggaaaa ccaatatttt     180
caatctgcta tttggtcagg atttatcaaa gttaagaaga gtgatgaata cactttgct      240 acttccgctg ataatcatgt aacaatgtgg gtagatgacc aagaagtgat taataaagct     300
tctaattcta acaaaatcag attagaaaaa ggaagattat atcaaataaa aattcaatat     360
```

```
caacgagaaa atcctactga aaaaggattg gatttcaagt tgtactggac cgattctcaa    420
aataaaaaag aagtgatttc tagtgataac ttacaattgc cagaattaaa acaaaaatct    480
tcgaactcaa gaaaaagcg aagtacaagt gctggaccta cggttccaga ccgtgacaat    540
gatggaatcc ctgattcatt agaggtagaa ggatatacgg ttgatgtcaa aaataaaaga    600
acttttcttt caccatggat ttctaatatt catgaaaaga aaggattaac caaatataaa    660
tcatctcctg aaaatggag cacggcttct gatccgtaca gtgatttcga aaaggttaca    720
ggacggattg ataagaatgt atcaccagag gcaagacacc cccttgtggc agct         774
```

<210> SEQ ID NO 5
<211> LENGTH: 487
<212> TYPE: PRT
<213> ORGANISM: Artificial Sequence
<220> FEATURE:
<223> OTHER INFORMATION: Description of Artificial Sequence: Fusion
      protein

<400> SEQUENCE: 5

```
Glu Val Lys Gln Glu Asn Arg Leu Leu Asn Glu Ser Glu Ser Ser Ser
  1               5                  10                  15

Gln Gly Leu Leu Gly Tyr Tyr Phe Ser Asp Leu Asn Phe Gln Ala Pro
             20                  25                  30

Met Val Val Thr Ser Ser Thr Thr Gly Asp Leu Ser Ile Pro Ser Ser
         35                  40                  45

Glu Leu Glu Asn Ile Pro Ser Glu Asn Gln Tyr Phe Gln Ser Ala Ile
     50                  55                  60

Trp Ser Gly Phe Ile Lys Val Lys Lys Ser Asp Glu Tyr Thr Phe Ala
 65                  70                  75                  80

Thr Ser Ala Asp Asn His Val Thr Met Trp Val Asp Asp Gln Glu Val
                 85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285
```

-continued

```
Ile Ser Lys Asn Thr Ser Thr Ser Arg Thr His Thr Ser Glu Val His
290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
            325                 330                 335

Ser Leu Ser Leu Ala Gly Glu Arg Thr Trp Ala Glu Thr Met Gly Leu
        340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
            405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Gly Lys Thr Lys Gln Leu
        435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr
            485
```

<210> SEQ ID NO 6
<211> LENGTH: 1461
<212> TYPE: DNA
<213> ORGANISM: Artificial Sequence
<220> FEATURE:
<223> OTHER INFORMATION: Description of Artificial Sequence: DNA
      sequence used to encode SEQ ID NO: 5

<400> SEQUENCE: 6

```
gaagttaaac aggagaaccg gttattaaat gaatcagaat caagttccca ggggttacta     60
ggatactatt ttagtgattt gaattttcaa gcacccatgg tggttacttc ttctactaca    120
ggggatttat ctattcctag ttctgagtta gaaaatattc catcggaaaa ccaatatttt    180
caatctgcta tttggtcagg atttatcaaa gttaagaaga gtgatgaata cattttgct     240 acttccgctg ataatcatgt aacaatgtgg gtagatgacc aagaagtgat taataaagct    300
tctaattcta acaaaatcag attagaaaaa ggaagattat atcaaataaa aattcaatat    360
caacgagaaa atcctactga aaaggattg gatttcaagt tgtactggac cgattctcaa    420
aataaaaaag aagtgatttc tagtgataac ttacaactgc agaattaaa acaaaaatct    480 tcgaactcaa gaaaaaagcg aagtacaagt gctggaccta cggttccaga ccgtgacaat    540
gatggaatcc ctgattcatt agaggtagaa ggatatacgg ttgatgtcaa aaataaaaga    600
acttttcttt caccatggat ttctaatatt catgaaaaga aaggattaac caaatataaa    660
tcatctcctg aaaaatggag cacggcttct gatccgtaca gtgatttcga aaaggttaca    720
ggacggattg ataagaatgt atcaccagag gcaagacacc cccttgtggc agcttatccg    780
attgtacatg tagatatgga gaatattatt ctctcaaaaa atgaggatca atccacacag    840
aatactgata gtgaaacgag aacaataagt aaaaaatactt ctacaagtag gacacatact    900
```

-continued

```
agtgaagtac atggaaatgc agaagtgcat gcgtcgttct ttgatattgg tgggagtgta    960
tctgcaggat ttagtaattc gaattcaagt acggtcgcaa ttgatcattc actatctcta   1020 gcagggaaa gaacttgggc tgaaacaatg gtttaaata ccgctgatac agcaagatta    1080
aatgccaata ttagatatgt aaatactggg acggctccaa tctacaacgt gttaccaacg   1140
acttcgttag tgttaggaaa aaatcaaaca ctcgcgacaa ttaaagctaa ggaaaaccaa   1200
ttaagtcaaa tacttgcacc taataattat tatccttcta aaaacttggc gccaatcgca   1260
ttaaatgcac aagacgattt cagttctact ccaattacaa tgaattacaa tcaatttctt   1320
gagttagaaa aaacgaaaca attaagatta gatacggatc aagtatatgg gaatatagca   1380
acatacaatt ttgaaaatgg aagagtgagg gtggatacag gctcgaactg gagtgaagtg   1440
ttaccgcaaa ttcaagaaac a                                             1461
```

<210> SEQ ID NO 7
<211> LENGTH: 318
<212> TYPE: PRT
<213> ORGANISM: Artificial Sequence
<220> FEATURE:
<223> OTHER INFORMATION: Description of Artificial Sequence: Fusion
      protein

<400> SEQUENCE: 7

```
Ser Ala Gly Pro Thr Val Pro Asp Arg Asp Asn Asp Gly Ile Pro Asp
  1               5                  10                  15

Ser Leu Glu Val Glu Gly Tyr Thr Val Asp Val Lys Asn Lys Arg Thr
                 20                  25                  30

Phe Leu Ser Pro Trp Ile Ser Asn Ile His Glu Lys Lys Gly Leu Thr
             35                  40                  45

Lys Tyr Lys Ser Ser Pro Glu Lys Trp Ser Thr Ala Ser Asp Pro Tyr
         50                  55                  60

Ser Asp Phe Glu Lys Val Thr Gly Arg Ile Asp Lys Asn Val Ser Pro
 65                  70                  75                  80

Glu Ala Arg His Pro Leu Val Ala Ala Tyr Pro Ile Val His Val Asp
                 85                  90                  95

Met Glu Asn Ile Ile Leu Ser Lys Asn Glu Asp Gln Ser Thr Gln Asn
                100                 105                 110

Thr Asp Ser Glu Thr Arg Thr Ile Ser Lys Asn Thr Ser Thr Ser Arg
            115                 120                 125

Thr His Thr Ser Glu Val His Gly Asn Ala Glu Val His Ala Ser Phe
        130                 135                 140

Phe Asp Ile Gly Gly Ser Val Ser Ala Gly Phe Ser Asn Ser Asn Ser
145                 150                 155                 160

Ser Thr Val Ala Ile Asp His Ser Leu Ser Leu Ala Gly Glu Arg Thr
                165                 170                 175

Trp Ala Glu Thr Met Gly Leu Asn Thr Ala Asp Thr Ala Arg Leu Asn
                180                 185                 190

Ala Asn Ile Arg Tyr Val Asn Thr Gly Thr Ala Pro Ile Tyr Asn Val
            195                 200                 205

Leu Pro Thr Thr Ser Leu Val Leu Gly Lys Asn Gln Thr Leu Ala Thr
        210                 215                 220

Ile Lys Ala Lys Glu Asn Gln Leu Ser Gln Ile Leu Ala Pro Asn Asn
225                 230                 235                 240

Tyr Tyr Pro Ser Lys Asn Leu Ala Pro Ile Ala Leu Asn Ala Gln Asp
                245                 250                 255
```

```
Asp Phe Ser Ser Thr Pro Ile Thr Met Asn Tyr Asn Gln Phe Leu Glu
            260                 265                 270

Leu Glu Lys Thr Lys Gln Leu Arg Leu Asp Thr Asp Gln Val Tyr Gly
        275                 280                 285

Asn Ile Ala Thr Tyr Asn Phe Glu Asn Gly Arg Val Arg Val Asp Thr
    290                 295                 300

Gly Ser Asn Trp Ser Glu Val Leu Pro Gln Ile Gln Glu Thr
305                 310                 315

<210> SEQ ID NO 8
<211> LENGTH: 954
<212> TYPE: DNA
<213> ORGANISM: Artificial Sequence
<220> FEATURE:
<223> OTHER INFORMATION: Description of Artificial Sequence: DNA
      sequence used to encode SEQ ID NO: 7

<400> SEQUENCE: 8
agtgctggac ctacggttcc agaccgtgac aatgatggaa tccctgattc attagaggta      60
gaaggatata cggttgatgt caaaaataaa agaactttc tttcaccatg gatttctaat     120
attcatgaaa agaaaggatt aaccaaatat aaatcatctc ctgaaaaatg gagcacggct     180
tctgatccgt acagtgattt cgaaaaggtt acaggacgga ttgataagaa tgtatcacca     240
gaggcaagac accccttgt ggcagcttat ccgattgtac atgtagatat ggagaatatt     300
attctctcaa aaaatgagga tcaatccaca cagaatactg atagtgaaac gagaacaata     360
agtaaaaata cttctacaag taggacacat actagtgaag tacatggaaa tgcagaagtg     420
catgcgtcgt tctttgatat tggtgggagt gtatctgcag gatttagtaa ttcgaattca     480
agtacggtcg caattgatca ttcactatct ctagcagggg aaagaacttg gctgaaaaca     540
atgggtttaa ataccgctga tacagcaaga ttaaatgcca atattagata tgtaaatact     600
gggacggctc caatctacaa cgtgttacca acgacttcgt tagtgttagg aaaaaatcaa     660
acactcgcga caattaaagc taaggaaaac caattaagtc aaatacttgc acctaataat     720
tattatcctt ctaaaaactt ggcgccaatc gcattaaatg cacaagacga tttcagttct     780
actccaatta caatgaatta caatcaattt cttgagttag aaaaaacgaa acaattaaga     840
ttagatacgg atcaagtata tggaatatat gcaacataca attttgaaaa tggaagagtg     900
agggtggata caggctcgaa ctggagtgaa gtgttaccgc aaattcaaga aaca           954

<210> SEQ ID NO 9
<211> LENGTH: 426
<212> TYPE: PRT
<213> ORGANISM: Artificial Sequence
<220> FEATURE:
<223> OTHER INFORMATION: Description of Artificial Sequence: Fusion
      protein

<400> SEQUENCE: 9

Ser Ala Gly Pro Thr Val Pro Asp Arg Asp Asn Asp Gly Ile Pro Asp
1               5                  10                  15

Ser Leu Glu Val Glu Gly Tyr Thr Val Asp Val Lys Asn Lys Arg Thr
            20                  25                  30

Phe Leu Ser Pro Trp Ile Ser Asn Ile His Glu Lys Lys Gly Leu Thr
        35                  40                  45

Lys Tyr Lys Ser Ser Pro Glu Lys Trp Ser Thr Ala Ser Asp Pro Tyr
    50                  55                  60

Ser Asp Phe Glu Lys Val Thr Gly Arg Ile Asp Lys Asn Val Ser Pro
65                  70                  75                  80
```

```
Glu Ala Arg His Pro Leu Val Ala Ala Tyr Pro Ile Val His Val Asp
             85                  90                  95

Met Glu Asn Ile Ile Leu Ser Lys Asn Glu Asp Gln Ser Thr Gln Asn
            100                 105                 110

Thr Asp Ser Glu Thr Arg Thr Ile Ser Lys Asn Thr Ser Thr Ser Arg
        115                 120                 125

Thr His Thr Ser Glu Val His Gly Asn Ala Glu Val His Ala Ser Phe
    130                 135                 140

Phe Asp Ile Gly Gly Ser Val Ser Ala Gly Phe Ser Asn Ser Asn Ser
145                 150                 155                 160

Ser Thr Val Ala Ile Asp His Ser Leu Ser Leu Ala Gly Glu Arg Thr
                165                 170                 175

Trp Ala Glu Thr Met Gly Leu Asn Thr Ala Asp Thr Ala Arg Leu Asn
            180                 185                 190

Ala Asn Ile Arg Tyr Val Asn Thr Gly Thr Ala Pro Ile Tyr Asn Val
        195                 200                 205

Leu Pro Thr Thr Ser Leu Val Leu Gly Lys Asn Gln Thr Leu Ala Thr
    210                 215                 220

Ile Lys Ala Lys Glu Asn Gln Leu Ser Gln Ile Leu Ala Pro Asn Asn
225                 230                 235                 240

Tyr Tyr Pro Ser Lys Asn Leu Ala Pro Ile Ala Leu Asn Ala Gln Asp
                245                 250                 255

Asp Phe Ser Ser Thr Pro Ile Thr Met Asn Tyr Asn Gln Phe Leu Glu
            260                 265                 270

Leu Glu Lys Thr Lys Gln Leu Arg Leu Asp Thr Asp Gln Val Tyr Gly
        275                 280                 285

Asn Ile Ala Thr Tyr Asn Phe Glu Asn Gly Arg Val Arg Val Asp Thr
    290                 295                 300

Gly Ser Asn Trp Ser Glu Val Leu Pro Gln Ile Gln Glu Thr Thr Ala
305                 310                 315                 320

Arg Ile Ile Phe Asn Gly Lys Asp Leu Asn Leu Val Glu Arg Arg Ile
                325                 330                 335

Ala Ala Val Asn Pro Ser Asp Pro Leu Glu Thr Thr Lys Pro Asp Met
            340                 345                 350

Thr Leu Lys Glu Ala Leu Lys Ile Ala Phe Gly Phe Asn Glu Pro Asn
        355                 360                 365

Gly Asn Leu Gln Tyr Gln Gly Lys Asp Ile Thr Glu Phe Asp Phe Asn
    370                 375                 380

Phe Asp Gln Gln Thr Ser Gln Asn Ile Lys Asn Gln Leu Ala Glu Leu
385                 390                 395                 400

Asn Ala Thr Asn Ile Tyr Thr Val Leu Asp Lys Ile Lys Leu Asn Ala
                405                 410                 415

Lys Met Asn Ile Leu Ile Arg Asp Lys Arg
            420                 425

<210> SEQ ID NO 10
<211> LENGTH: 1278
<212> TYPE: DNA
<213> ORGANISM: Artificial Sequence
<220> FEATURE:
<223> OTHER INFORMATION: Description of Artificial Sequence: DNA
      sequence used to encode SEQ ID NO: 9

<400> SEQUENCE: 10
agtgctggac ctacggttcc agaccgtgac aatgatggaa tccctgattc attagaggta      60
gaaggatata cggttgatgt caaaaataaa agaacttttc tttcaccatg gatttctaat     120
```

-continued

```
attcatgaaa agaaaggatt aaccaaatat aaatcatctc ctgaaaaatg gagcacggct      180
tctgatccgt acagtgattt cgaaaaggtt acaggacgga ttgataagaa tgtatcacca      240
gaggcaagac accccttgt ggcagcttat ccgattgtac atgtagatat ggagaatatt       300
attctctcaa aaatgagga tcaatccaca cagaatactg atagtgaaac gagaacaata       360
agtaaaaata cttctacaag taggacacat actagtgaag tacatggaaa tgcagaagtg      420
catgcgtcgt tctttgatat tggtgggagt gtatctgcag gatttagtaa ttcgaattca      480
agtacggtcg caattgatca ttcactatct ctagcagggg aaagaacttg ggctgaaaca      540
atgggtttaa ataccgctga tacagcaaga ttaaatgcca atattagata tgtaaatact      600
gggacggctc caatctacaa cgtgttacca acgacttcgt tagtgttagg aaaaaatcaa      660
acactcgcga caattaaagc taaggaaaac caattaagtc aaatacttgc acctaataat      720
tattatcctt ctaaaaactt ggcgccaatc gcattaaatg cacaagacga tttcagttct      780
actccaatta caatgaatta caatcaattt cttgagttag aaaaaacgaa acaattaaga      840
ttagatacgg atcaagtata tgggaatata gcaacataca attttgaaaa tggaagagtg      900
agggtggata caggctcgaa ctggagtgaa gtgttaccgc aaattcaaga aacaactgca      960
cgtatcattt ttaatggaaa agatttaaat ctggtagaaa ggcggatagc ggcggttaat     1020
cctagtgatc cattagaaac gactaaaccg gatatgacat taaagaagc ccttaaaata     1080 gcatttggat ttaacgaacc gaatggaaac ttacaatatc aagggaaaga cataaccgaa     1140
tttgatttta atttcgatca acaaacatct caaaatatca agaatcagtt agcggaatta     1200
aacgcaacta acatatatac tgtattagat aaaatcaaat taaatgcaaa aatgaatatt     1260
ttaataagag ataaacgt                                                    1278
```

<210> SEQ ID NO 11
<211> LENGTH: 595
<212> TYPE: PRT
<213> ORGANISM: Artificial Sequence
<220> FEATURE:
<223> OTHER INFORMATION: Description of Artificial Sequence: Fusion
      protein

<400> SEQUENCE: 11

```
Glu Val Lys Gln Glu Asn Arg Leu Leu Asn Glu Ser Glu Ser Ser Ser
 1               5                  10                  15

Gln Gly Leu Leu Gly Tyr Tyr Phe Ser Asp Leu Asn Phe Gln Ala Pro
             20                  25                  30

Met Val Thr Ser Ser Thr Thr Gly Asp Leu Ser Ile Pro Ser Ser
         35                  40                  45

Glu Leu Glu Asn Ile Pro Ser Glu Asn Gln Tyr Phe Gln Ser Ala Ile
     50                  55                  60

Trp Ser Gly Phe Ile Lys Val Lys Lys Ser Asp Glu Tyr Thr Phe Ala
 65                  70                  75                  80

Thr Ser Ala Asp Asn His Val Thr Met Trp Val Asp Asp Gln Glu Val
                 85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160
```

```
Ser Asn Ser Arg Lys Lys Arg Ser Thr Ser Ala Gly Pro Thr Val Pro
            165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
            195                 200                 205

Asn Ile His Glu Lys Lys Gly Leu Thr Lys Tyr Lys Ser Ser Pro Glu
            210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
            245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Glu Thr Arg Thr
            275                 280                 285

Ile Ser Lys Asn Thr Ser Thr Ser Arg Thr His Thr Ser Glu Val His
            290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
            325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
            370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
            405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
            435                 440                 445

Arg Leu Asp Thr Asp Gln Val Tyr Gly Asn Ile Ala Thr Tyr Asn Phe
            450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
            485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
            515                 520                 525

Ile Ala Phe Gly Phe Asn Glu Pro Asn Gly Asn Leu Gln Tyr Gln Gly
            530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
            565                 570                 575
```

Val Leu Asp Lys Ile Lys Leu Asn Ala Lys Met Asn Ile Leu Ile Arg
            580                 585                 590

Asp Lys Arg
        595

<210> SEQ ID NO 12
<211> LENGTH: 1785
<212> TYPE: DNA
<213> ORGANISM: Artificial Sequence
<220> FEATURE:
<223> OTHER INFORMATION: Description of Artificial Sequence: DNA
      sequence used to encode SEQ ID NO: 11

<400> SEQUENCE: 12

| | | | | | |
|---|---|---|---|---|---|
| gaagttaaac | aggagaaccg | gttattaaat | gaatcagaat | caagttccca | ggggttacta | 60 |
| ggatactatt | ttagtgattt | gaattttcaa | gcacccatgg | tggttacctc | ttctactaca | 120 |
| ggggatttat | ctattcctag | ttctgagtta | gaaaatattc | catcggaaaa | ccaatatttt | 180 |
| caatctgcta | tttggtcagg | atttatcaaa | gttaagaaga | gtgatgaata | cataattgct | 240 |
| acttccgctg | ataatcatgt | aacaatgtgg | gtagatgacc | aagaagtgat | taataaagct | 300 |
| tctaattcta | acaaaatcag | attagaaaaa | ggaagattat | atcaaataaa | aattcaatat | 360 |
| caacgagaaa | atcctactga | aaaaggattg | gatttcaagt | tgtactggac | cgattctcaa | 420 |
| aataaaaaag | aagtgatttc | tagtgataac | ttacaattgc | cagaattaaa | acaaaaatct | 480 |
| tcgaactcaa | gaaaaagcg | agtacaagt | gctggaccta | cggttccaga | ccgtgacaat | 540 |
| gatggaatcc | ctgattcatt | agaggtagaa | ggatatacgg | ttgatgtcaa | aaataaaaga | 600 |
| acttttcttt | caccatggat | ttctaatatt | catgaaaaga | aaggattaac | caaatataaa | 660 |
| tcatctcctg | aaaaatggag | cacggcttct | gatccgtaca | gtgatttcga | aaaggttaca | 720 |
| ggacggattg | ataagaatgt | atcaccagag | gcaagacacc | cccttgtggc | agcttatccg | 780 |
| attgtacatg | tagatatgga | gaatattatt | ctctcaaaaa | atgaggatca | atccacacag | 840 |
| aatactgata | gtgaaacgag | aacaataagt | aaaaatactt | ctacaagtag | gacacatact | 900 |
| agtgaagtac | atgaaatgc | agaagtgcat | gcgtcgttct | ttgatattgg | tgggagtgta | 960 |
| tctgcaggat | ttagtaattc | gaattcaagt | acggtcgcaa | ttgatcattc | actatctcta | 1020 |
| gcagggaaa | gaacttgggc | tgaaacaatg | ggtttaaata | ccgctgatac | agcaagatta | 1080 |
| aatgccaata | ttagatatgt | aaatactggg | acggctccaa | tctacaacgt | gttaccaacg | 1140 |
| acttcgttag | tgttaggaaa | aaatcaaaca | ctcgcgacaa | ttaaagctaa | ggaaaaccaa | 1200 |
| ttaagtcaaa | tacttgcacc | taataattat | tatccttcta | aaaacttggc | gccaatcgca | 1260 |
| ttaaatgcac | aagacgattt | cagttctact | ccaattacaa | tgaattacaa | tcaatttctt | 1320 |
| gagttagaaa | aaacgaaaca | attaagatta | gatacggatc | aagtatatgg | gaatatagca | 1380 |
| acatacaatt | ttgaaaatgg | aagagtgagg | gtggatacag | gctcgaactg | gagtgaagtg | 1440 |
| ttaccgcaaa | ttcaagaaac | aactgcacgt | atcattttta | atggaaaaga | tttaaatctg | 1500 |
| gtagaaaggc | ggatagcggc | ggttaatcct | agtgatccat | tagaaacgac | taaaccggat | 1560 |
| atgacattaa | aagaagccct | taaaatagca | tttggattta | acgaaccgaa | tggaaactta | 1620 |
| caatatcaag | ggaaagacat | aaccgaattt | gattttaatt | tcgatcaaca | aacatctcaa | 1680 |
| aatatcaaga | atcagttagc | ggaattaaac | gcaactaaca | tatatactgt | attagataaa | 1740 |
| atcaaattaa | atgcaaaaat | gaatatttta | ataagagata | aacgt | | 1785 |

```
<210> SEQ ID NO 13
<211> LENGTH: 735
<212> TYPE: PRT
<213> ORGANISM: Artificial Sequence
<220> FEATURE:
<223> OTHER INFORMATION: Description of Artificial Sequence: Fusion
      protein

<400> SEQUENCE: 13

Glu Val Lys Gln Glu Asn Arg Leu Leu Asn Glu Ser Glu Ser Ser
 1               5                  10                  15

Gln Gly Leu Leu Gly Tyr Tyr Phe Ser Asp Leu Asn Phe Gln Ala Pro
            20                  25                  30

Met Val Thr Ser Ser Thr Thr Gly Asp Leu Ser Ile Pro Ser Ser
            35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
    210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
        275                 280                 285

Ile Ser Lys Asn Thr Ser Thr Ser Arg Thr His Thr Ser Glu Val His
    290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
        355                 360                 365
```

Thr Gly Thr Ala Pro Ile Tyr Asn Val Leu Pro Thr Thr Ser Leu Val
370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
        435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
                500                 505                 510

Pro Leu Glu Thr Thr Lys Pro Asp Met Thr Leu Lys Glu Ala Leu Lys
            515                 520                 525

Ile Ala Phe Gly Phe Asn Glu Pro Asn Gly Asn Leu Gln Tyr Gln Gly
530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
                580                 585                 590

Asp Lys Arg Phe His Tyr Asp Arg Asn Asn Ile Ala Val Gly Ala Asp
            595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
                660                 665                 670

Lys Thr Phe Ile Asp Phe Lys Lys Tyr Asn Asp Lys Leu Pro Leu Tyr
            675                 680                 685

Ile Ser Asn Pro Asn Tyr Lys Val Asn Val Tyr Ala Val Thr Lys Glu
        690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735

<210> SEQ ID NO 14
<211> LENGTH: 2208
<212> TYPE: DNA
<213> ORGANISM: Artificial Sequence
<220> FEATURE:
<223> OTHER INFORMATION: Description of Artificial Sequence: DNA
      sequence used to encode SEQ ID NO: 13

<400> SEQUENCE: 14

```
gaagttaaac aggagaaccg gttattaaat gaatcagaat caagttccca ggggttacta      60
ggatactatt ttagtgattt gaattttcaa gcacccatgg tggttacctc ttctactaca     120
ggggatttat ctattcctag ttctgagtta gaaaatattc catcggaaaa ccaatatttt     180
caatctgcta tttggtcagg atttatcaaa gttaagaaga gtgatgaata tacatttgct     240
acttccgctg ataatcatgt aacaatgtgg gtagatgacc aagaagtgat taataaagct     300
tctaattcta acaaaatcag attagaaaaa ggaagattat atcaaataaa aattcaatat     360
caacgagaaa atcctactga aaaggattg gatttcaagt tgtactggac cgattctcaa     420
aataaaaaag aagtgatttc tagtgataac ttacaattgc cagaattaaa acaaaaatct     480
tcgaactcaa gaaaaaagcg aagtacaagt gctggaccta cggttccaga ccgtgacaat     540
gatggaatcc ctgattcatt agaggtagaa ggatatacgg ttgatgtcaa aaataaaaga     600
acttttcttt caccatggat ttctaatatt catgaaaaga aaggattaac caaatataaa     660
tcatctcctg aaaaatggag cacggcttct gatccgtaca gtgatttcga aaaggttaca     720
ggacggattg ataagaatgt atcaccagag gcaagacacc cccttgtggc agcttatccg     780
attgtacatg tagatatgga gaatattatt ctctcaaaaa atgaggatca atccacacag     840
aatactgata gtgaaacgag aacaataagt aaaaatactt ctacaagtag gacacatact     900
agtgaagtac atggaaatgc agaagtgcat gcgtcgttct ttgatattgg tgggagtgta     960
tctgcaggat ttagtaattc gaattcaagt acggtcgcaa ttgatcattc actatctcta    1020
gcagggaaa gaacttgggc tgaaacaatg ggtttaaata ccgctgatac agcaagatta    1080
aatgccaata ttagatatgt aaatactggg acggctccaa tctacaacgt gttaccaacg    1140
acttcgttag tgttaggaaa aaatcaaaca ctcgcgacaa ttaaagctaa ggaaaaccaa    1200
ttaagtcaaa tacttgcacc taataattat tatccttcta aaaacttggc gccaatcgca    1260
ttaaatgcac aagacgattt cagttctact ccaattacaa tgaattacaa tcaatttctt    1320
gagttagaaa aaacgaaaca attaagatta gatacggatc aagtatatgg gaatatagca    1380
acatacaatt ttgaaaatgg aagagtgagg gtggatacag gctcgaactg gagtgaagtg    1440
ttaccgcaaa ttcaagaaac aactgcacgt atcattttta atggaaaaga tttaaatctg    1500
gtagaaaggc ggatagcggc ggttaatcct agtgatccat tagaaacgac taaaccggat    1560
atgcattaa aagaagccct taaaatagca tttggattta acgaaccgaa tggaaactta    1620
caatatcaag ggaaagacat aaccgaattt gattttaatt tcgatcaaca acatctcaa    1680
aatatcaaga atcagttagc ggaattaaac gcaactaaca tatatactgt attagataaa    1740
atcaaattaa atgcaaaaat gaatatttta ataagagata aacgttttca ttatgataga    1800
aataacatag cagttggggc ggatgagtca gtagttaagg aggctcatag agaagtaatt    1860
aattcgtcaa cagagggatt attgttaaat attgataagg atataagaaa atatattca    1920
ggttatattg tagaaattga agatactgaa gggcttaaag aagttataaa tgacagatat    1980
gatatgttga atatttctag tttacggcaa gatggaaaaa catttataga ttttaaaaaa    2040
tataatgata aattaccgtt atatataagt aatcccaatt ataaggtaaa tgtatatgct    2100
gttactaaag aaaacactat tattaatcct agtgagaatg gggatactag taccaacggg    2160
atcaagaaaa ttttaatctt ttctaaaaaa ggctatgaga taggataa                 2208
```

```
<210> SEQ ID NO 15
<211> LENGTH: 140
<212> TYPE: PRT
<213> ORGANISM: Bacillus anthracis

<400> SEQUENCE: 15

Phe His Tyr Asp Arg Asn Asn Ile Ala Val Gly Ala Asp Glu Ser Val
 1               5                  10                  15

Val Lys Glu Ala His Arg Glu Val Ile Asn Ser Ser Thr Glu Gly Leu
                20                  25                  30

Leu Leu Asn Ile Asp Lys Asp Ile Arg Lys Ile Leu Ser Gly Tyr Ile
            35                  40                  45

Val Glu Ile Glu Asp Thr Glu Gly Leu Lys Glu Val Ile Asn Asp Arg
        50                  55                  60

Tyr Asp Met Leu Asn Ile Ser Ser Leu Arg Gln Asp Gly Lys Thr Phe
 65                  70                  75                  80

Ile Asp Phe Lys Lys Tyr Asn Asp Lys Leu Pro Leu Tyr Ile Ser Asn
                 85                  90                  95

Pro Asn Tyr Lys Val Asn Val Tyr Ala Val Thr Lys Glu Asn Thr Ile
                100                 105                 110

Ile Asn Pro Ser Glu Asn Gly Asp Thr Ser Thr Asn Gly Ile Lys Lys
            115                 120                 125

Ile Leu Ile Phe Ser Lys Lys Gly Tyr Glu Ile Gly
        130                 135                 140

<210> SEQ ID NO 16
<211> LENGTH: 423
<212> TYPE: DNA
<213> ORGANISM: Artificial Sequence
<220> FEATURE:
<223> OTHER INFORMATION: Description of Artificial Sequence: DNA coding
      sequence for domain 4.

<400> SEQUENCE: 16
tttcattatg atagaaataa catagcagtt ggggcggatg agtcagtagt taaggaggct      60
catagagaag taattaattc gtcaacagag ggattattgt taaatattga taaggatata    120
agaaaaatat tatcaggtta tattgtagaa attgaagata ctgaagggct taaagaagtt    180
ataaatgaca gatatgatat gttgaatatt tctagtttac ggcaagatgg aaaaacattt    240
atagatttta aaaatataa tgataaatta ccgttatata taagtaatcc caattataag    300
gtaaatgtat atgctgttac taaagaaaac actattatta atcctagtga gaatggggat    360
actagtacca acgggatcaa gaaaatttta atctttctta aaaaaggcta tgagatagga    420
taa                                                                   423
```

EXPRESSION SYSTEM

CROSS REFERENCE TO RELATED PATENT APPLICATIONS

The present application is a divisional application of U.S. patent application Ser. No. 10/332,282 filed Apr. 11, 2003 now U.S. Pat. No. 7,537,771, which claims priority to Great Britain Application No. 0016702.3 filed on Jul. 8, 2000 and International Application No. PCT/GB01/03065 filed on Jul. 6, 2001 and published in English as International Publication No. WO 02/04646 A1 on Jan. 17, 2002, the entire contents of which are incorporated herein by reference.

The present invention relates to polypeptides which produce an immune response which is protective against infection by *Bacillus anthracis*, to methods of producing these, to recombinant *Escherischia coli* cells, useful in the methods, and to nucleic acids and transformation vectors used.

Present systems for expressing PA for vaccine systems use protease deficient *Bacillus subtilis* as the expression host. Although such systems are acceptable in terms of product quantity and purity, there are significant drawbacks. Firstly, regulatory authorities are generally unfamiliar with this host, and licensing decisions may be delayed as a result. More importantly, the currently used strains of *Bacillus subtilis* produce thermostable spores which require the use of a dedicated production plant.

WO00/02522 describes in particular VEE virus replicons which express PA or certain immunogenic fragments.

*E. coli* is well known as an expression system for a range of human vaccines. While the ability to readily ferment *E. coli* to very high cellular densities makes this bacterium an ideal host for the expression of many proteins, previous attempts to express and purify recombinant PA from *E. coli* cytosol have been hindered by low protein yields and proteolytic degradation (Singh et al., J. Biol. Chem. (1989) 264; 11099-11102, Vodkin et al., Cell (1993) 34; 693-697 and Sharma et al., Protein Expr. purif. (1996), 7, 33-38).

A strategy for overexpressing PA as a stable, soluble protein in the *E. coli* cytosol has been described recently (Willhite et al., Protein and Peptide Letters, (1998), 5; 273-278). The strategy adopted is one of adding an affinity tag sequence to the N terminus of PA, which allows a simple purification system.

A problem with this system is that it requires a further downstream processing step in order to remove the tag before the PA can be used.

Codon optimisation is a technique which is now well known and used in the design of synthetic genes. There is a degree of redundancy in the genetic code, in so far as most amino acids are coded for by more than one codon sequence. Different organisms utilise one or other of these different codons preferentially. By optimising codons, it is generally expected that expression levels of the particular protein will be enhanced.

This is generally desirable, except where, as in the case of PA, higher expression levels will result in proteolytic degradation and/or cell toxicity. In such cases, elevating expression levels might be counter-productive and result in significant cell toxicity.

Surprisingly however, the applicants have found that this is not the case in *E. coli* and that in this system, codon optimisation results in expression of unexpectedly high levels of recombinant PA, irrespective of the presence or absence of proteolytic enzymes within the strain.

Furthermore, it would appear that expression of a protective domain of PA does not inhibit expression in *E. coli*.

The crystal structure of native PA has been elucidated (Petosa C., et al. Nature 385: 833-838, 1997) and shows that PA consists of four distinct and functionally independent domains: domain 1, divided into 1a, 1-167 amino acids and 1b, 168-258 amino acids; domain 2, 259-487 amino acids; domain 3, 488-595 amino acids and domain 4, 596-735 amino acids.

The applicants have identified that certain domains appear to produce surprisingly good protective effects when used in isolation, in fusion proteins or in combination with each other.

According to the present invention there is provided an immunogenic reagent which produces an immune response which is protective against *Bacillus anthracis*, said reagent comprising one or more polypeptides which together represent up to three domains of the full length Protective Antigen (PA) of *B. anthracis* or variants of these, and at least one of said domains comprises domain 1 or domain 4 of PA or a variant thereof.

Specifically, the reagent will comprise mixtures of polypeptides or fusion peptides wherein individual polypeptides comprise one of more individual domains of PA.

In particular, the reagent comprises polypeptide(s) comprising domain 1 or domain 4 of PA or a variant thereof, in a form other than full length PA. Where present, domains are suitably complete, in particular domain 1 is present in its entirety.

The term "polypeptide" used herein includes proteins and peptides.

As used herein, the expression "variant" refers to sequences of amino acids which differ from the basic sequence in that one or more amino acids within the sequence are deleted or substituted for other amino acids, but which still produce an immune response which is protective against *Bacillus anthracis*. Amino acid substitutions may be regarded as "conservative" where an amino acid is replaced with a different amino acid with broadly similar properties. Non-conservative substitutions are where amino acids are replaced with amino acids of a different type. Broadly speaking, fewer non-conservative substitutions will be possible without altering the biological activity of the polypeptide. Suitably variants will be at least 60% identical, preferably at least 75% identical, and more preferably at least 90% identical to the PA sequence.

In particular, the identity of a particular variant sequence to the PA sequence may be assessed using the multiple alignment method described by Lipman and Pearson, (Lipman, D. J. & Pearson, W. R. (1985) Rapid and Sensitive Protein Similarity Searches, Science, vol 227, pp 1435-1441). The "optimised" percentage score should be calculated with the following parameters for the Lipman-Pearson algorithm: ktup=1, gap penalty=4 and gap penalty length=12. The sequences for which similarity is to be assessed should be used as the "test sequence" which means that the base sequence for the comparison, (SEQ ID NO 1), should be entered first into the algorithm.

Preferably, the reagent of the invention includes a polypeptide which has the sequence of domain 1 and/or domain 4 of wild-type PA.

A particularly preferred embodiment of the invention comprises domain 4 of the PA of *B. anthracis*.

These domains comprise the following sequences shown in the following Table 1.

TABLE 1

| Domain | Amino acids of full-length PA* |
|---|---|
| 4 | 596-735 |
| 1 | 1-258 |

These amino acids numbers refer to the sequence as shown in Welkos et al. Gene 69 (1988) 287-300 and are illustrated hereinafter as SEQ ID NOs 15 (FIG. 4) and 3 (FIG. 3) respectively.

Domain 1 comprises two regions, designated 1a and 1b. Region 1a comprises amino acids 1-167 whereas region 1b is from amino acid 168-258. It appears that region 1a is important for the production of a good protective response, and the full domain may be preferred.

In a particularly preferred embodiment, a combination of domains 1 and 4 or protective regions thereof, are used as the immunogenic reagent which gives rise to an immune response protective against *B. anthracis*. This combination, for example as a fusion peptide, may be expressed using the expression system of the invention as outlined hereinafter.

When domain 1 is employed, it is suitably fused to domain 2 of the PA sequence, and may preferably be fused to domain 2 and domain 3.

Such combinations and their use in prophylaxis or therapy forms a further aspect of the invention.

Suitably the domains described above are part of a fusion protein, preferably with an N-terminal glutathione-s-transferase protein (GST). The GST not only assists in the purification of the protein, it may also provide an adjuvant effect, possibly as a result of increasing the size.

The polypeptides of the invention are suitably prepared by conventional methods. For example, they may be synthesised or they may be prepared using recombinant DNA technology. In particular, nucleic acids which encode said domains are included in an expression vector, which is used to transform a host cell. Culture of the host cell followed by isolation of the desired polypeptide can then be carried out using conventional methods. Nucleic acids, vectors and transformed cells used in these methods form a further aspect of the invention.

Generally speaking, the host cells used will be those that are conventionally used in the preparation of PA, such as *Bacillus subtilis*.

The applicants have found surprisingly that the domains either in isolation or in combination, maybe successfully expressed in *E. coli* under certain conditions.

Thus, the present invention further provides a method for producing an immunogenic polypeptide which produces an immune response which is protective against *B. anthracis*, said method comprising transforming an *E. coli* host with a nucleic acid which encodes either (a) the protective antigen (PA) of *Bacillus anthracis* or a variant thereof which can produce a protective immune response, or (b) a polypeptide comprising at least one protective domain of the protective antigen (PA) of *Bacillus anthracis* or a variant thereof which can produce a protective immune response as described above, culturing the transformed host and recovering the polypeptide therefrom, provided that where the polypeptide is the protective antigen (PA) of *Bacillus anthracis* or a variant thereof which can produce a protective immune response, the percentage of guanidine and cytosine residues within the said nucleic acid is in excess of 35%.

Using these options, high yields of product can be obtained using a favoured expression host.

A table showing codons and the frequency with which they appear in the genomes of *Escherichia coli* and *Bacillus anthracis* is shown in FIG. 1. It is clear that guanidine and cytosine appear much more frequently in *E. coli* than *B. anthracis*. Analysis of the codon usage content reveals the following:

| Species | 1$^{st}$ letter of Codon GC | 2nd letter of Codon GC | 3rd letter of Codon GC | Total GC content |
|---|---|---|---|---|
| *E. coli* | 58.50% | 40.70% | 54.90% | 51.37% |
| *B. anthracis* | 44.51% | 31.07% | 25.20% | 33.59% |

Thus it would appear that codons which are favoured by *E. coli* are those which include guanidine or cytosine where possible.

By increasing the percentage of guanidine and cytosine nucleotides in the sequence used to encode the immunogenic protein over that normally found in the wild-type *B. anthracis* gene, the codon usage will be such that expression in *E. coli* is improved.

Suitably the percentage of guanidine and cytosine residues within the coding nucleic acid used in the invention, at least where the polypeptide is the protective antigen (PA) of *Bacillus anthracis* or a variant thereof which can produce a protective immune response, is in excess of 40%, preferably in excess of 45% and most preferably from 50-52%.

High levels of expression of protective domains can be achieved, with using the wild-type *B. anthracis* sequence encoding these units. However, the yields may be improved further by increasing the GC % of the nucleic acid as described above.

In a particular embodiment, the method involves the expression of PA of *B. anthracis*.

Further according to the present invention, there is provided a recombinant *Escherischia coli* cell which has been transformed with a nucleic acid which encodes the protective antigen (PA) of *Bacillus anthracis* or a variant thereof which can produce a protective immune response, and wherein the percentage of guanidine and cytosine residues within the nucleic acid is in excess of 35%.

As before, suitably the percentage of guanidine and cytosine residues within the coding nucleic acid is in excess of 40%, preferably in excess of 45% and most preferably from 50-52%.

Suitably, the nucleic acid used to transform the *E. coli* cells of the invention is a synthetic gene. In particular, the nucleic acid is of SEQ ID NO 1 as shown in FIG. 2 or a modified form thereof.

The expression "modified form" refers to other nucleic acid sequences which encode PA or fragments or variants thereof which produce a protective immune response but which utilise some different codons, provided the requirement for the percentage GC content in accordance with the invention is met. Suitable modified forms will be at least 80% similar, preferably 90% similar and most preferably at least 95% similar to SEQ ID NO 1. In particular, the nucleic acid comprises SEQ ID NO 1.

In an alternative embodiment, the invention provides a recombinant *Escherischia coli* cell which has been transformed with a nucleic acid which encodes a protective domain of the protective antigen (PA) of *Bacillus anthracis* or a variant thereof which can produce a protective immune response.

Preferably, the nucleic acid encodes domain 1 or domain 4 of *B. anthracis*.

Further according to the invention there is provided a method of producing immunogenic polypeptide which produces an immune response which is protective against *B. anthracis*, said method comprising culturing a cell as described above and recovering the desired polypeptide from the culture. Such methods are well known in the art.

In yet a further aspect, the invention provides an *E. coli* transformation vector comprising a nucleic acid which encodes the protective antigen (PA) of *Bacillus anthracis* or a variant thereof which can produce a protective immune response, and wherein the percentage of guanidine and cytosine residues within the nucleic acid is in excess of 35%.

A still further aspect of the invention comprises an *E. coli* transformation vector comprising a nucleic acid which encodes a protective domain of the protective antigen (PA) of *Bacillus anthracis* or a variant thereof which can produce a protective immune response.

Suitable vectors for use in the transformation of *E. coli* are well known in the art. For example, the T7 expression system provides good expression levels. However a particularly preferred vector comprises pAG163 obtainable from Avecia (UK).

A nucleic acid of SEQ ID NO 1 or a variant thereof which encodes PA and which has at 35%, preferably at least 40%, more preferably at least 45% and most preferably from 50-52% GC content form a further aspect of the invention.

If desired, PA of the variants, or domains can be expressed as a fusion to another protein, for example a protein which provides a different immunity, a protein which will assist in purification of the product or a highly expressed protein (e.g. thioredoxin, GST) to ensure good initiation of translation.

Optionally, additional systems will be added such as T7 lysozyme to the expression system, to improve the repression of the system, although, in the case of the invention, the problems associated with cell toxicity have not been noted.

Any suitable *E. coli* strain can be employed in the process of the invention. Strains which are deficient in a number of proteases (e.g. Ion⁻, ompT⁻) are available, which would be expected to minimise proteolysis. However, the applicants have found that there is no need to use such strains to achieve good yields of product and that other known strains such as K12 produce surprisingly high product yields.

Fermentation of the strain is generally carried out under conventional conditions as would be understood in the art. For example, fermentations can be carried out as batch cultures, preferably in large shake flasks, using a complex medium containing antibiotics for plasmid maintenance and with addition of IPTG for induction.

Suitably cultures are harvested and cells stored at −20° C. until required for purification.

Suitable purification schemes for *E. coli* PA (or variant or domain) expression can be adapted from those used in *B. subtilis* expression. The individual purification steps to be used will depend on the physical characteristics of recombinant PA. Typically an ion exchange chromatography separation is carried out under conditions which allow greatest differential binding to the column followed by collection of fractions from a shallow gradient. In some cases, a single chromatographic step may be sufficient to obtain product of the desired specification.

Fractions can be analysed for the presence of the product using SDS PAGE or Western blotting as required.

As illustrated hereinafter, the successful cloning and expression of a panel of fusion proteins representing intact or partial domains of rPA has been achieved. The immunogenicity and protective efficacy of these fusion proteins against STI spore challenge has been assessed in the A/J mouse model.

All the rPA domain proteins were immunogenic in A/J mice and conferred at least partial protection against challenge compared to the GST control immunised mice. The carrier protein, GST attached to the N-terminus of the domain proteins, did not impair the immunogenicity of the fusion proteins either in vivo, shown by the antibody response stimulated in immunised animals, or in vitro as the fusion proteins could be detected with anti-rPA antisera after Western blotting, indicating that the GST tag did not interfere with rPA epitope recognition. Immunisation with the larger fusion proteins produced the highest titres. In particular, mice immunised with the full length GST 1-4 fusion protein produced a mean serum anti-rPA concentration approximately eight times that of the rPA immunised group (FIG. 5). Immunisation of mice with rPA domains 1-4 with the GST cleaved off, produced titres of approximately one half those produced by immunisation with the fusion protein. Why this fusion protein should be much more immunogenic is unclear. It is possible that the increased size of this protein may have an adjuvantising effect on the immune effector cells. It did not stimulate this response to the same extent in the other fusion proteins and any adjuvantising effect of the GST tag did not enhance protection against challenge as the cleaved proteins were similarly protective to their fusion protein counterparts.

Despite having good anti-rPA titres, some breakthrough in protection at the lower challenge level of $10^2$ MLD's, occurred in the groups immunised with GST1, cleaved 1, GST1b-2, GST1b-3 and GST1-3 and immunisation with these proteins did not prolong the survival time of those mice that did succumb to challenge, compared with the GST control immunised mice. This suggests that the immune response had not been appropriately primed by these proteins to achieve full resistance to the infection. As has been shown in other studies in mice and guinea pigs (Little S. F. et al. 1986. Infect. Immun. 52: 509-512, Turnbull P. C. B., et al., 1986. Infect. Immun. 52: 356-363) there is no precise correlation between antibody titre to PA and protection against challenge. However a certain threshold of antibody is required for protection (Cohen S et. al., 2000 Infect. Immun: 68: 4549-4558), suggesting that cell mediated components of the immune response are also required to be stimulated for protection (Williamson 1989).

GST1, GST1b-2 and GST1-2 were the least stable fusion proteins produced, as shown by SDS-Page and Western blotting results, possibly due to the proteins being more susceptible to degradation in the absence of domain 3, and this instability may have resulted in the loss of protective epitopes.

The structural conformation of the proteins may also be important for stimulating a protective immune response. The removal of Domain 1a from the fusion proteins gave both reduced antibody titres and less protection against challenge, when compared to their intact counterparts GST1-2 and GST1-3. Similarly, mice immunised with GST 1 alone were partially protected against challenge, but when combined with domain 2, as the GST1-2 fusion protein, full protection was seen at the $10^2$ MLD challenge level. However the immune response stimulated by immunisation with the GST1-2 fusion protein was insufficient to provide full protection against the higher $10^3$ MLD's challenge level, which again could be due to the loss of protective epitopes due to degradation of the protein.

All groups immunised with truncates containing domain 4, including GST 4 alone, cleaved 4 alone and a mixture of two individually expressed domains, GST 1 and GST 4 were fully protected against challenge with $10^3$ MLDs of STI spores (Table 1). Brossier et al showed a decrease in protection in mice immunised with a mutated strain of B. anthracis that expressed PA without domain 4 (Brossier F., et al. 2000. Infect. Immun. 68: 1781-1786) and this was confirmed in this study, where immunisation with GST 1-3 resulted in breakthrough in protection despite good antibody titres. These data indicate that domain 4 is the immunodominant sub-unit of PA. Domain 4 represents the 139 amino acids of the carboxy terminus of the PA polypeptide. It contains the host cell receptor binding region (Little S. F. et al., 1996 Microbiology 142: 707-715), identified as being in and near a small loop located between amino acid residues 679-693 (Varughese M., et al. 1999 Infect. Immun. 67:1860-1865).

Therefore it is essential for host cell intoxication as it has been demonstrated that forms of PA expressed containing mutations (Varughese 1999 supra.) or deletions (Brossier 1999 supra.) in the region of domain 4 are non-toxic. The crystal structure of PA shows domain 4, and in particular a 19 amino acid loop of the domain (703-722), to be more exposed than the other three domains which are closely associated with each other (Petosa 1997 supra.). This structural arrangement may make domain 4 the most prominent epitope for recognition by immune effector cells, and therefore fusion proteins containing domain 4 would elicit the most protective immune response.

This investigation has further elucidated the role of PA in the stimulation of a protective immune response demonstrating that protection against anthrax infection can be attributed to individual domains of PA.

The invention will now be particularly described by way of example, with reference to the accompanying drawings in which:

FIG. 1 is a Table of codon frequencies found within E. coli and B. anthracis;

FIG. 2 shows the sequence of a nucleic acid according to the invention, which encodes PA of B. subtilis, as published by Welkos et al supra; and FIG. 3 shows SEQ ID NOs 3-14, which are amino acid and DNA sequences used to encode various domains or combinations of domains of PA as detailed hereinafter;

Figure 5:
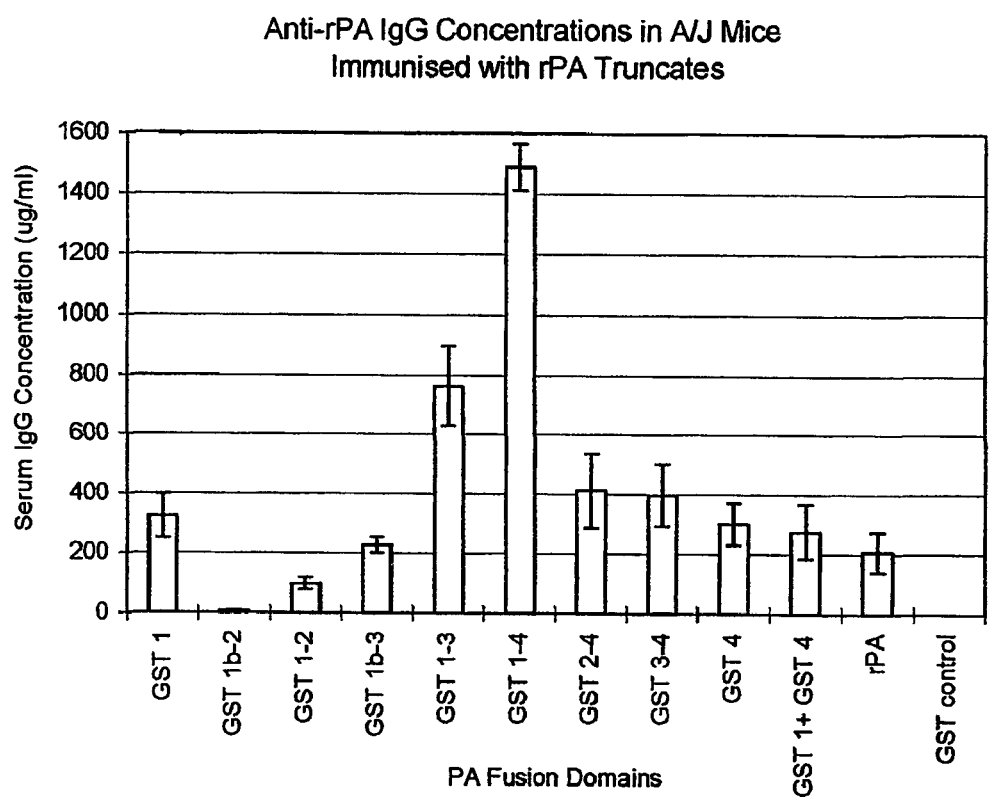

FIG. 4 shows SEQ ID NOs 15-16 which are the amino acid and DNA sequences of domain 4 of PA respectively; and FIG. 5 is a table showing anti-rPA IgG concencentration, 37 days post primary immunisation, from A/J mice immunised intramuscularly on days 1 and 28 with 10 µg of fusion protein included PA fragment; results shown are mean±sem of samples taken from 5 mice per treatment group.

EXAMPLE 1

Investigation into Expression in E. coli rPA expression plasmid pAG163::rPA has been modified to substitute $Km^R$ marker for original $Tc^R$ gene. This plasmid has been transformed into expression host E. coli BLR (DE3) and expression level and solubility assessed. This strain is deficient in the intracellular protease La (Ion gene product) and the outer membrane protease OmpT.

Expression studies did not however show any improvement in the accumulation of soluble protein in this strain compared to Ion+ K12 host strains (i.e. accumulation is prevented due to excessive proteolysis). It was concluded that any intracellular proteolysis of rPA was not due to the action of La protease.

EXAMPLE 2

Fermentation Analysis

Further analysis of the fermentation that was done using the K12 strain UT5600 (DE3) pAG163::rPA.

It was found that the rPA in this culture was divided between the soluble and insoluble fractions (estimated 350 mg/L insoluble, 650 mg/L full length soluble). The conditions used (37° C., 1 mM IPTG for induction) had not yielded any detectable soluble rPA in shake flask cultures and given the results described in Example 1 above, the presence of a large amount of soluble rPA is surprising. Nevertheless it appears that manipulation of the fermentation, induction and point of harvest may allow stable accumulation of rPA in E. coli K12 expression strains.

EXAMPLE 3

A sample of rPA was produced from material initially isolated as insoluble inclusion bodies from the UT5600 (DE3) pAG163::rPA fermentation. Inclusion bodies were washed-twice with 25 mM Tris-HCl pH8 and once with same buffer +2M urea. They were then solubilized in buffer +8M urea and debris pelleted. Urea was removed by dilution into 25 mM Tris-HCl pH8 and static incubation overnight at 4° C. Diluted sample was applied to Q sepharose column and protein eluted with NaCl gradient. Fractions containing highest purity rPA were pooled, aliquoted and frozen at −70° C. Testing of this sample using 4-12% MES-SDS NuPAGE gel against a known standard indicated that it is high purity and low in endotoxin contamination.

EXAMPLE 4

Further Characterisation of the Product

N terminal sequencing of the product showed that the N-terminal sequence consisted of

MEVKQENRLL        (SEQ ID NO 2)

This confirmed that the product was as expected with initiator methionine left on.

The material was found to react in Western blot; MALDI-MS on the sample indicated a mass of approx 82 700 (compared to expected mass of 82 915). Given the high molecular mass and distance from mass standard used (66 KDa), this is considered an indication that material does not have significant truncation but does not rule out microheterogeneity within the sample.

EXAMPLE 5

Testing of Individual Domains of PA

Individual domains of PA were produced as recombinant proteins in E. coli as fusion proteins with the carrier protein glutathione-s-transferase (GST), using the Pharmacia pGEX-6P-3 expression system. The sequences of the various domains and the DNA sequence used to encode them are attached herewith as FIG. 3. The respective amino acid and DNA sequences are provided in Table 2 below.

These fusion proteins were used to immunise A/J mice (Harlan Olac) intra-muscularly with 10 µg of the respective fusion protein adsorbed to 20% v/v alhydrogel in a total volume of 100 µl.

Animals were immunised on two occasions and their development of protective immunity was determined by challenge with spores of B. anthracis (STI strain) at the indicated dose levels. The table below shows survivors at 14 days post-challenge.

Challenge Level in Spores/Mouse

| Domains | Amino acid SEQ ID NO | DNA SEQ ID NO | $5 \times 10^4$ | $9 \times 10^4$ | $9 \times 10^5$ | $1 \times 10^6$ | $5 \times 10^6$ |
|---|---|---|---|---|---|---|---|
| GST-1 | 3 | 4 | 4/4 | 3/5 | | | |
| GST-1 + 2 | 5 | 6 | 4/4; 5/5 | 4/5; 5/5 | | | |
| GST-1b + 2 | 7 | 8 | 2/5 | 1/5 | | | |
| GST-1b + 2 + 3 | 9 | 10 | 2/5 | 3/5 | | | |
| GST-1 + 2 + 3 | 11 | 12 | Nd | 4/5 | 3/5 | | |
| GST-1 + 2 + 3 + 4 | 13 | 14 | Nd | 5/5 | 5/5 | | |
| 1 + 2 + 3 + 4 | 13 | 14 | Nd | Nd | | 5/5 | 5/5 |

The data shows that a combination of all 4 domains of PA, whether presented as a fusion protein with GST or not, were protective up to a high challenge level. Removal of domain 4, leaving 1+2+3, resulted in breakthrough at the highest challenge level tested, $9 \times 10^5$. Domains 1+2 were as protective as a combination of domains 1+2+3 at $9 \times 10^4$ spores. However, removal of domain 1a to leave a GST fusion with domains $1b_+2$, resulted in breakthrough in protection at the highest challenge level tested ($9 \times 10^{4)}$ which was only slightly improved by adding domain 3.

The data indicates that the protective immunity induced by PA can be attributed to individual domains (intact domain 1 and domain 4) or to combinations of domains taken as permutations from all 4 domains.

The amino acid sequence and a DNA coding sequence for domain 4 is shown in FIG. 4 as SEQ ID NOs 15 and 16 respectively.

EXAMPLE 6

Further Testing of Domains as Vaccines

DNA encoding the PA domains, amino acids 1-259, 168-488, 1-488, 168-596, 1-596, 260-735, 489-735, 597-735 and 1-735 (truncates GST1, GST1b-2, GST1-2, GST1b-3, GST1-3, GST2-4, GST3-4, GST4 and GST1-4 respectively) were PCR amplified from B. anthracis Sterne DNA and cloned in to the XhoI/BamHI sites of the expression vector pGEX-6-P3 (Amersham-Pharmacia) downstream and in frame of the lac promoter. Proteins produced using this system were expressed as fusion proteins with an N-terminal glutathione-s-transferase protein (GST). Recombinant plasmid DNA harbouring the DNA encoding the PA domains was then transformed in to E. coli BL21 for protein expression studies.

E. coli BL21 harbouring recombinant pGEX-6-P3 plasmids were cultured in L-broth containing 50 µg/ml ampicillin, 30 µg/ml chloramphenicol and 1% w/v glucose. Cultures were incubated with shaking (170 rev min$^{-1}$) at 30° C. to an $A_{600\ nm}$ 0.4, prior to induction with 0.5 mM IPTG. Cultures were incubated for a further 4 hours, followed by harvesting by centrifugation at 10 000 rpm for 15 minutes.

Initial extraction of the PA truncates-fusion proteins indicated that they were produced as inclusion bodies. Cell pellets were resuspended in phosphate buffered saline (PBS) and sonicated 4×20 seconds in an iced water bath. The suspension was centrifuged at 15 000 rpm for 15 minutes and cell pellets were then urea extracted, by suspension in 8M urea with stirring at room temperature for 1 hour. The suspension was centrifuged for 15 minutes at 15000 rpm and the supernatant dialysed against 100 mM Tris pH 8 containing 400 mM L-arginine and 0.1 mM EDTA, prior to dialysis into PBS.

The successful refolding of the PA truncate-fusion proteins allowed them to be purified on a glutathione Sepharose CL-4B affinity column. All extracts (with the exception of truncate GST1b-2, amino acid residues 168-487) were applied to a 15 ml glutathione Sepharose CL-4B column (Amersham-Parmacia), previously equilibrated with PBS and incubated, with rolling, overnight at 4° C. The column was washed with PBS and the fusion protein eluted with 50 mM Tris pH7, containing 150 mM NaCl, 1 mM EDTA and 20 mM reduced glutathione. Fractions containing the PA truncates, identified by SDS-PAGE analysis, were pooled and dialysed against PBS. Protein concentration was determined using BCA (Perbio).

However truncate GST1b-2 could not be eluted from the glutathione sepharose CL-4B affinity column using reduced glutathione and was therefore purified using ion exchange chromatography. Specifically, truncate GST1b-2 was dialysed against 20 mM Tris pH8, prior to loading onto a HiTrap Q column (Amersham-Parmacia), equilibrated with the same buffer. Fusion protein was eluted with an increasing NaCl gradient of 0-1 M in 20 mM Tris pH8. Fractions containing the GST-protein were pooled, concentrated and loaded onto a HiLoad 26/60 Superdex 200 gel filtration column (Amersham-Parmacia), previously equilibrated with PBS. Fractions containing fusion protein were pooled and the protein concentration determined by BCA (Perbio). Yields were between 1 and 43 mg per litre of culture.

The molecular weight of the fragments and their recognition by antibodies to PA was confirmed using SDS PAGE and Western Blotting. Analysis of the rPA truncates by SDS Page and Western blotting showed protein bands of the expected sizes. Some degradation in all of the rPA truncates investigated was apparent showing similarity with recombinant PA expressed in B. subtilis. The rPA truncates GST1, GST1b-2 and GST1-2 were particularly susceptible to degradation in the absence of domain 3. This has similarly been reported for rPA constructs containing mutations in domain 3, that could not be purified from B. anthracis culture supernatants (Brossier 1999), indicating that domain 3 may stabilise domains 1 and 2.

Female, specific pathogen free A/J mice (Harlan UK) were used in this study as these are a consistent model for anthrax infection (Welkos 1986). Mice were age matched and seven weeks of age at the start of the study.

A/J mice were immunised on days 1 and 28 of the study with 10 µg of fusion protein adsorbed to 20% of 1.3% v/v Alhydrogel (HCl Biosector, Denmark) in a total volume of 100 µl of PBS. Groups immunised with rPA from B. subtilis (Miller 1998), with recombinant GST control protein, or fusion proteins encoding domains 1, 4 and 1-4 which had the GST tag removed, were also included. Immunising doses were administered intramuscularly into two sites on the hind legs. Mice were blood sampled 37 days post primary immunisation for serum antibody analysis by enzyme linked immunosorbant assay (ELISA).

Microtitre plates (Immulon 2, Dynex Technologies) were coated, overnight at 4° C. with 5 μg/ml rPA, expressed from *B. subtilis* (Miller 1998), in PBS except for two rows per plate which were coated with 5 μg/ml anti-mouse Fab (Sigma, Poole, Dorset). Plates were washed with PBS containing 1% v/v Tween 20 (PBS-T) and blocked with 5% w/v skimmed milk powder in PBS (blotto) for 2 hours at 37° C. Serum, double-diluted in 1% blotto, was added to the rPA coated wells and was assayed in duplicate together with murine IgG standard (Sigma) added to the anti-fab coated wells and incubated overnight at 4° C. After washing, horse-radish peroxidase conjugated goat anti-mouse IgG (Southern Biotechnology Associates Inc.), diluted 1 in 2000 in PBS, was added to all wells, and incubated for 1 hour at 37° C. Plates were washed again before addition of the substrate 2,2'-Azinobis (3-ethylbenzthiazoline-sulfonic acid) (1.09 mM ABTS, Sigma). After 20 minutes incubation at room temperature, the absorbance of the wells at 414 nm was measured (Titertek Multiscan, ICN Flow). Standard curves were calculated using Titersoft version 3.1c software. Titres were presented as μg IgG per ml serum and group means±standard error of the mean (sem) were calculated. The results are shown in FIG. 5.

All the rPA truncates produced were immunogenic and stimulated mean serum anti-rPA IgG concentrations in the A/J mice ranging from 6 μg per ml, for the GST1b-2 truncate immunised group, to 1488 μg per ml, in the GST 1-4 truncate immunised group (FIG. 5). The GST control immunised mice had no detectable antibodies to rPA.

Mice were challenged with *B. anthracis* STI spores on day 70 of the immunisation regimen. Sufficient STI spores for the challenge were removed from stock, washed in sterile distilled water and resuspended in PBS to a concentration of $1 \times 10^7$ and $1 \times 10^6$ spores per ml. Mice were challenged intraperitoneally with 0.1 ml volumes containing $1 \times 10^6$ and $1 \times 10^5$ spores per mouse, respectively, and were monitored for 14 day post challenge to determine their protected status. Humane end-points were strictly observed so that any animal displaying a collection of clinical signs which together indicated it had a lethal infection, was culled. The numbers of immunised mice which survived 14 days post challenge are shown in Table 3.

TABLE 3

| | Challenge Level MLDs survivors/no. challenged (%) | |
|---|---|---|
| Domain | $10^2$ MLDs | $10^3$ MLDs |
| GST 1 | 3/5 (60) | 1/5 (20) |
| GST 1b-2 | 1/5 (20) | nd |
| GST 1-2 | 5/5 (100) | 3/5 (60) |
| GST 1b-3 | 3/5 (60) | nd |
| GST 1-3 | 4/5 (80) | nd |
| GST 1-4 | nd | 5/5 (100) |
| GST 2-4 | nd | 5/5 (100) |
| GST 3-4 | nd | 5/5 (100) |
| GST 4 | 5/5 (100) | 5/5 (100) |
| GST 1 + GST 4 | nd | 5/5 (100) |
| Cleaved 1 | 1/5 (20) | 2/5 |
| Cleaved 4 | 5/5 (100) | 5/5 |
| Cleaved 1-4 | nd | 5/5 |
| rPA | nd | 4/4 (100) |
| control | 0/5 (0) | 0/5 (0) |

1 MLD = aprox. $1 \times 10^3$ STI spores nd = not done

The groups challenged with $10^3$ MLD's of STI spores were all fully protected except for the GST1, GST1-2 and cleaved 1 immunised groups in which there was some breakthrough in protection, and the control group immunised with GST only, which all succumbed to infection with a mean time to death (MTTD) of 2.4±0.2 days. At the lower challenge level of $10^2$ MLD's the GST1-2, GST4 and cleaved 4-immunised groups were all fully protected, but there was some breakthrough in protection in the other groups. The mice that died in these groups had a MTTD of 4.5±0.2 days which was not significantly different from the GST control immunised group which all died with a MTTD of 4±0.4 days.

The invention claimed is:

1. A method for producing an immunogenic polypeptide which produces an immune response which is protective against *B. anthracis*, the method comprising transforming an *E. coli* host with a nucleic acid which encodes a protective antigen (PA) of *Bacillus anthracis* or a variant thereof which can produce a protective immune response, wherein GC content of the nucleic acid is at least 35%, and wherein the amino acid sequence of the variant of the PA of *Bacillus anthracis* is at least 60% identical to the amino acid sequence encoded by SEQ ID NO:1.

2. The method of claim 1, wherein the nucleic acid encodes the PA of *Bacillus anthracis*.

3. The method of claim 1, wherein the GC content within the nucleic acid is in excess of 45%.

4. The method of claim 3, wherein the GC content within the nucleic acid is from 50-52%.

5. A method of producing a polypeptide which produces an immune response which is protective against *Bacillus anthracis*, the method comprising culturing a recombinant *Escherichia coli* cell obtained by transforming an *E. coli* cell with a nucleic acid which encodes a protective antigen (PA) of *B. anthracis* or a variant thereof which can produce a protective immune response, and recovering the protective polypeptide from the culture, wherein the GC content of the nucleic acid is at least 35%, and wherein the nucleic acid which encodes the variant of the PA of *Bacillus anthracis* is at least 80% similar to SEQ ID NO:1.

6. The method of claim 5, wherein the nucleic acid encodes the PA of *Bacillus anthracis*.

7. The method of claim 5, wherein the GC content within the nucleic acid is in excess of 45%.

8. The method of claim 5, wherein the nucleic acid encodes the PA of *Bacillus anthracis*.

9. A method for producing an immunogenic polypeptide which produces an immune response which is protective against *B. anthracis*, the method comprising transforming an *E. coli* host with a nucleic acid which encodes either (a) the protective antigen (PA) of *Bacillus anthracis*, or (b) a protective domain of the PA of *Bacillus anthracis*, culturing the transformed host and recovering the polypeptide therefrom,
wherein the GC content of the nucleic acid is at least 35%, and wherein the protective domain of the PA comprises at least one of domain 1, region 1b of domain 1, or domain 4 of the PA.

10. The method of claim 9, wherein the GC content within the nucleic acid is from 50-52%.

11. The method of claim 9, wherein the GC content within the nucleic acid is in excess of 45%.

12. The method of claim 9, wherein the GC content within the nucleic acid is from 50-52%.

13. A method for producing an immunogenic polypeptide which produces an immune response which is protective against *B. anthracis*, the method comprising transforming an *E. coli* host with a nucleic acid which encodes a protective antigen (PA) of *Bacillus anthracis* or a variant thereof which can produce a protective immune response, wherein the GC content of the nucleic acid is at least 35%, wherein the nucleic acid which encodes the variant of the PA of *Bacillus anthracis* is at least 90% similar to SEQ ID NO:1.

14. The method of claim 13, wherein the nucleic acid encodes the PA of *Bacillus anthracis*.

15. The method of claim 13, wherein the GC content within the nucleic acid is in excess of 45%.

16. The method of claim 13, wherein the GC content within the nucleic acid is from 50-52%.

17. A method of producing a polypeptide which produces an immune response which is protective against *Bacillus anthracis*, the method comprising culturing a recombinant *Escherichia coli* cell obtained by transforming an *E. coli* cell with a nucleic acid which encodes a protective antigen (PA) of *B. anthracis* or a variant thereof which can produce a protective immune response, and recovering the protective polypeptide from the culture,
wherein the GC content of the nucleic acid is at least 35%, and wherein the amino acid sequence of the variant of the PA of *Bacillus anthracis* is at least 90% identical to the amino acid sequence encoded by SEQ ID NO:1.

18. The method of claim 17, wherein the nucleic acid encodes the PA of *Bacillus anthracis*.

19. The method of claim 17, wherein the GC content within the nucleic acid is in excess of 45%.

20. The method of claim 17, wherein the GC content within the nucleic acid is from 50-52%.

* * * * *